(12) United States Patent
Starck et al.

(10) Patent No.: US 7,465,744 B2
(45) Date of Patent: Dec. 16, 2008

(54) TRIAZOLE COMPOUNDS AND THE THERAPEUTIC USE THEREOF

(75) Inventors: Dorothea Starck, Ludwigshafen (DE); Hans-Jörg Treiber, Brühl (DE); Thomas Zierke, Böhl-Iggelheim (DE); Georg Kettschau, Berlin (DE); Hervé Geneste, Neuhofen (DE); Andreas Haupt, Schwetzingen (DE); Liliane Unger, Ludwigshafen (DE); Kai Blumbach, Steinen (DE); Dietmar Schöbel, Mannheim (DE); Hans-Jurgen Teschendorf, Dudenhofen (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 0 days.

(21) Appl. No.: 10/544,550

(22) PCT Filed: Feb. 5, 2004

(86) PCT No.: PCT/EP2004/001072

§ 371 (c)(1),
(2), (4) Date: Jun. 7, 2006

(87) PCT Pub. No.: WO2004/069830

PCT Pub. Date: Aug. 19, 2004

(65) Prior Publication Data

US 2006/0241137 A1    Oct. 26, 2006

(30) Foreign Application Priority Data

Feb. 6, 2003    (DE) ................ 103 04 870

(51) Int. Cl.
*A61K 31/41* (2006.01)
*C07D 401/02* (2006.01)

(52) U.S. Cl. ............... 514/307; 514/383; 546/148; 548/266.4

(58) Field of Classification Search ......... 546/148; 548/266.4; 514/307, 383

See application file for complete search history.

(56) References Cited

U.S. PATENT DOCUMENTS 6,124,294 A    9/2000    Hellendahl et al.
6,214,822 B1    4/2001    Treiber et al.
6,472,392 B1    10/2002    Starck et al.
6,579,892 B1    6/2003    Starck et al.

FOREIGN PATENT DOCUMENTS

| DE | 44 25 144 | 1/1999 |
|----|-----------|--------|
| WO | WO 97/25324 | 1/1996 |
| WO | WO 99/02503 | 7/1997 |
| WO | WO 00/42036 A1 | 7/2000 |

OTHER PUBLICATIONS

Levant, The D3 Dopamine Receptor: Neurobiology and Potential Clinical Relevance, Pharmacological Reviews, vol. 49, No. 3, pp. 231-252, 1997.*
J C Schwartz et al. "The Dopamine D3 Receptor As A Target For Antipsychotics" Novel Antipsychotic Drugs, New York 1992, pp. 135-144.
Mukta Dooley et al "Pramipexole" Drugs & Aging, Jun. 1998, vol. 12, pp. 495-514.
J N Joyce et al "Dopamine D3 Receptor As A Therapeutic Target For Antipsychotic And Antiparkinsonian Drugs" Pharmacology & Therapeutics, 2001, vol. 90 pp. 231-259.
P Sokoloff et al. "Localization And Function Of The D3 Dopamine Receptor" Drug and Research 1992, vol. 42(1) No. 2a, pp. 224-230.
P Sokoloff et al "Molecular Cloning And Characterization Of A Novel Dopamine Receptor (D3) As A Target For Neuroleptics" Nature Sep. 13, 1990, vol. 347, pp. 146-151.

* cited by examiner

*Primary Examiner*—Zinna N Davis
(74) *Attorney, Agent, or Firm*—Dykema Gossett PLLC

(57) ABSTRACT

The invention relates to triazole compounds of general formula (I), wherein A, B, $R^1$, $R^2$, $R^3$ and $R^4$ have the meaning cited in claim 1. The invention also relates to a pharmaceutical agent containing at least one compound of general formula (I) in addition to the use of the compound (I) for producing a pharmaceutical agent for treating illnesses, responding to the effects of dopamine-$D_3$-receptor antagonists or dopamine-$D_3$-receptor agonists, especially for treating disorders in the central nervous system.

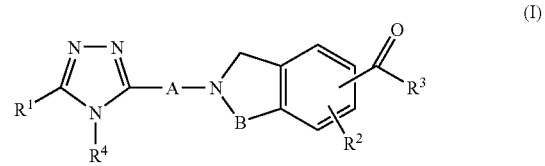

16 Claims, No Drawings

TRIAZOLE COMPOUNDS AND THE THERAPEUTIC USE THEREOF

CROSS-REFERENCE TO RELATED APPLICATION

This application is a Section 371 application of PCT/EP2004/01072, filed Feb. 5, 2004 which claims the priority of DE 10304870.7, filed Feb. 6, 2003.

DESCRIPTION

The present invention relates to triazole compounds and to the therapeutic use thereof. The compounds have valuable therapeutic properties and are suitable in particular for the treatment of disorders which respond to modulation of the dopamine $D_3$ receptor.

Neurons receive their information inter alia via G protein-coupled receptors. There are numerous substances which exert their effect via these receptors. One of these is dopamine. Confirmed findings about the presence of dopamine and its physiological function as neurotransmitter have been published. Disturbances in the dopaminergic transmitter system result in disorders of the central nervous system which include, for example, schizophrenia, depression or Parkinson's disease. These and other disorders are treated with medicaments which interact with the dopamine receptors.

Until 1990, two subtypes of dopamine receptors were clearly defined pharmacologically, namely the $D_1$ and $D_2$ receptors. More recently, a third subtype has been found, namely the $D_3$ receptor, which appears to mediate some effects of antipsychotics and antiparkinsonian drugs (J. C. Schwartz et al., The Dopamine $D_3$ Receptor as a Target for Antipsychotics, in Novel Antipsychotic Drugs, H. Y. Meltzer, Ed. Raven Press, New York 1992, pages 135-144; M. Dooley et al., Drugs and Aging 1998, 12, 495-514 N. Joyce "Dopamine $D_3$-Receptors as a Therapeutic Target for Antipsychotic and Antiparkinsonian Drugs" Pharmacology and Therapeutics, 2001, 90, pp. 231-259).

Dopamine receptors are now divided into two families, firstly the $D_2$ group consisting of $D_2$, $D_3$ and $D_4$ receptors, and secondly the $D_1$ group consisting of $D_1$ and $D_5$ receptors. Whereas $D_1$ and $D_2$ receptors are widespread, the expression of $D_3$ receptors by contrast appears to be regioselective. Thus, these receptors are preferentially found in the limbic system, the projecting regions of the mesolimbic dopamine system, especially in the nucleus accumbens, but also in other regions such as amygdala. Because of this comparatively regioselective expression, $D_3$ receptors are regarded as a target with few side effects, and it is assumed that a selective $D_3$ ligand ought to have the properties of known antipsychotics but not their dopamine $D_2$ receptor-mediated neurological side effects (P. Sokoloff et al., Localization and Function of the $D_3$ Dopamine Receptor, *Arzneim. Forsch./Drug Res.* 42(1), 224 (1992); P. Sokoloff et al. Molecular Cloning and Characterization of a Novel Dopamine Receptor ($D_3$) as a Target for Neuroleptics, *Nature*, 347, 146 (1990)).

Triazole compounds having dopamine $D_3$ receptor affinity are disclosed in DE 4425144, WO 97/25324 and WO 99/02503.

In addition, WO 00/42036 discloses triazole compounds of the general formula

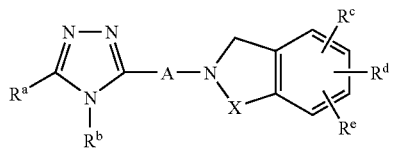

in which
A is $C_4$-$C_{10}$-alkylene or $C_3$-$C_{10}$-alkylene which includes at least one group Z which is selected from O, S, NR', CONR', COO, CO, $C_3$-$C_6$-cycloalkylene and a double or triple bond, where R' is, for example, H or $C_1$-$C_6$-alkyl which is optionally substituted by OH, $C_1$-$C_4$-alkoxy, halogen or phenyl,
X is $CH_2$ or $CH_2$—$CH_2$
$R^a$ may be inter alia an optionally substituted aromatic or heteroaromatic radical,
$R^b$ is H, $C_1$-$C_6$-alkyl which is optionally substituted by OH, $C_1$-$C_4$-alkoxy, halogen or phenyl, or $C_3$-$C_6$-cycloalkyl or phenyl;
$R^c$, $R^d$ and $R^e$ are independently of one another H, optionally substituted alkyl, OH, alkoxy, trifluoromethoxy, $OSO_2CF_3$, SH, alkylthio, alkenyl, alkynyl, halogen, CN, $NO_2$, $CO_2R'$, $SO_2R'$, $SO_2NR'R''$, $CONR'R''$, $NHSO_2R'$, $NR'R''$, a carbocyclic 5- or 6-membered, optionally substituted aromatic or nonaromatic ring or a heterocyclic 5- or 6-membered, optionally substituted aromatic or nonaromatic ring, where R' has the aforementioned meanings, R" has the meanings mentioned for R', or R' and R" form together with the nitrogen atom a 5- to 7-membered nitrogen heterocycle.

The triazole compounds disclosed in WO 00/42036 have a high affinity for dopamine $D_3$ receptors with, at the same time, high selectivity in relation to other dopamine receptors.

It is desirable to have access to selective dopamine $D_3$ receptor ligands which additionally have a high bio-availability and a high cerebral availability. Compounds having high bioavailability have the advantage that a given threshold concentration of the medicament at the site of action can be achieved with a lower dose to be administered orally. In addition, a higher concentration of the medicament at the site of action is achieved on administration of a given dose.

The invention is therefore based on the object of providing compounds which act as selective dopamine $D_3$ receptor ligands. The compounds ought additionally to have high bioavailability and high cerebral availability.

This object is surprisingly achieved by triazole compounds of the general formula I:

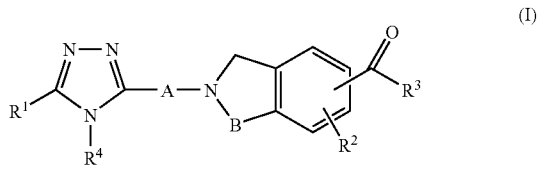

in which
A is $C_4$-$C_{10}$-alkylene or $C_3$-$C_{10}$-alkylene which includes at least one group Z which is selected from O, S, $NR^5$, $CONR^5$, COO and CO, where alkylene may also have a $C_3$-$C_6$-cycloalkylene group and/or a double or triple bond,
B is $CH_2$ or $CH_2$—$CH_2$;

$R^1$ is an aromatic radical which is selected from phenyl and a 5- or 6-membered heteroaromatic radical having 1, 2, 3 or 4 heteroatoms which are selected independently of one another from O, N and S, where the aromatic radical may have one or more, e.g. 1, 2 or 3, substituents which are selected independently of one another from $C_1$-$C_6$-alkyl which is optionally substituted by OH, $C_1$-$C_4$-alkoxy, halogen or phenyl, or $C_2$-$C_6$-alkenyl, $C_2$-$C_6$-alkynyl, $C_3$-$C_6$-cycloalkyl which is optionally substituted by halogen or $C_1$-$C_4$-alkyl, or halogen, CN, $OR^6$, $COOR^6$, $NR^7R^8$, $NO_2$, $SR^9$, $SO_2R^9$, $SO_2NR^7R^8$, $COR^{10}$, and phenyl which is optionally substituted by one or two radicals which are selected independently of one another from $C_1$-$C_4$-alkyl, $C_1$-$C_4$-alkoxy, $NR^7R^8$, CN, $CF_3$, $CHF_2$ or halogen, where phenyl and the heteroaromatic radical may also be fused to a 5 or 6-membered, aromatic or non-aromatic carbocycle;

$R^2$ is H, $C_1$-$C_6$-alkyl which is optionally substituted by OH, $C_1$-$C_4$-alkoxy, $C_1$-$C_4$-alkylthio, halogen or phenyl, or OH, $C_1$-$C_6$-alkoxy, $OCF_3$, $OCHF_2$, $OSO_2CF_3$, SH, $C_1$-$C_6$-alkylthio, $C_2$-$C_6$-alkenyl, $C_2$-$C_6$-alkynyl, halogen, CN or $NO_2$;

$R^3$ is $C_2$-$C_{10}$-alkyl, $C_1$-$C_6$-haloalkyl, $C_1$-$C_{10}$-alkyl which is substituted by $C_1$-$C_4$-alkoxy, $C_1$-$C_4$-alkylthio or phenyl which may in turn have one, two or three substituents selected from $C_1$-$C_4$-alkyl, $C_1$-$C_4$-haloalkyl, halogen, CN, $OR^6$, $COOR^6$, $NR^7R^8$, $NO_2$, $SR^9$, $SO_2R^9$, $SO_2NR^7R^8$, $COR^{10}$ and halogen, is $C_3$-$C_6$-cycloalkyl which is optionally substituted by halogen or $C_1$-$C_4$-alkyl, or is an aromatic radical which is selected from phenyl, naphthyl and a 5- or 6-membered heteroaromatic radical having 1, 2, or 3 heteroatoms which are selected independently of one another from O, N and S, where the aromatic radical may have one or two substituents which are selected independently of one another from $C_1$-$C_6$-alkyl, $C_1$-$C_6$-haloalkyl, $C_1$-$C_6$-alkoxy, halogen, CN, $COOR^6$, $NR^7R^8$, $NO_2$, $SO_2R^9$, $SO_2NR^7R^8$, $COR^{10}$, $CF_3$, $CHF_2$ or halogen, where $R^3$ may also be methyl if $R^1$ is a radical different from phenyl, in particular is an optionally substituted heteroaromatic radical;

$R^4$ is H, $C_1$-$C_6$-alkyl which is optionally substituted by OH, $C_1$-$C_4$-alkoxy or phenyl, or $C_1$-$C_6$-haloalkyl, $C_3$-$C_6$-cycloalkyl which is optionally substituted by $C_1$-$C_4$-alkyl or halogen, or phenyl;

$R^5$ is H, $C_1$-$C_6$-alkyl which is optionally substituted by OH, $C_1$-$C_4$-alkoxy or phenyl, or $C_1$-$C_6$-haloalkyl, phenyl or a $COR^6$ group;

$R^6$ to $R^{10}$ are independently of one another H, $C_1$-$C_6$-alkyl which is optionally substituted by OH, $C_1$-$C_4$-alkoxy or phenyl, or $C_1$-$C_6$-haloalkyl or phenyl, where $R^8$ may also be a $COR^{11}$ group in which $R^{11}$ has one of the meanings mentioned for $R^4$;

$R^7$ may also form together with $R^8$ a 5- or 6-membered saturated or unsaturated carbocycle which may have a heteroatom selected from O, S, N and $NR^{12}$ as ring member, where $R^{12}$ is hydrogen or $C_1$-$C_4$-alkyl, and by the physiologically tolerated salts of these compounds.

The inventive compounds of the formula I are selective dopamine $D_3$ receptor ligands. They are therefore suitable for the treatment of disorders which respond to their influencing, i.e. modulation of such ligands. Examples of such disorders are impairments and disorders of the central nervous system, especially affective disorders, neurotic disorders, stress disorders and somatoform disorders and psychoses, specifically schizophrenia and depression, and additionally disorders of renal function, especially those caused by diabetes mellitus (see WO 00/67847).

The invention therefore relates to the compounds I and to the use thereof for the treatment of such disorders, and for producing a medicament for the treatment of such disorders.

The invention also relates to a pharmaceutical composition (=medicament) comprising at least one compound of the formula I, where appropriate in the form of a physiologically tolerated salt of I, and where appropriate one or more physiologically tolerated carriers and/or excipients.

The aforementioned indications are treated according to the invention by using at least one compound of the general formula I having the meanings mentioned at the outset. If the compounds of the formula I have one or more centers of asymmetry, it is also possible to employ mixtures of enantiomers, especially racemates, mixtures of diastereomers, mixtures of tautomers, but preferably the respective substantially pure enantiomers, diastereomers and tautomers.

It is likewise possible to use physiologically tolerated salts of the compounds of the formula I, especially acid addition salts with physiologically tolerated acids. Examples of suitable physiologically tolerated organic and inorganic acids are hydrochloric acid, hydrobromic acid, phosphoric acid, sulfuric acid, oxalic acid, maleic acid, fumaric acid, lactic acid, tartaric acid, adipic acid or benzoic acid. Further acids which can be used are described in Fortschritte der Arzneimittelforschung, Volume 10, pages 224 et seq., Birkhäuser Verlag, Basle and Stuttgart, 1966.

$C_n$-$C_m$-Alkyl (also in radicals such as alkoxy, alkylthio, alkylamino etc.) means a straight-chain or branched alkyl group having n to m carbon atoms, e.g. 1 to 6 carbon atoms and in particular 1 to 4 carbon atoms. Examples of an alkyl group are methyl, ethyl, n-propyl, isopropyl, n-butyl, 2-butyl, isobutyl, tert-butyl, n-pentyl, 2-pentyl, neopentyl, n-hexyl and the like.

The alkyl group may have one or more substituents which are selected independently of one another from OH, $C_1$-$C_4$-alkoxy, halogen or phenyl. In the case of a halogen substituent, the alkyl group may include in particular 1, 2, 3 or 4 halogen atoms which may be present on one or more C atoms, preferably in the α- or ω-position. Groups of this type are also referred to hereinafter as haloalkyl. A preferred haloalkyl is fluoroalkyl or fluorochloroalkyl, in particular $CF_3$, $CHF_2$, $CF_2Cl$, $CH_2F$, $CH_2CF_3$.

In the case of hydroxyl-substituted alkyl, the alkyl group has in particular one hydroxyl group, such as, for example, hydroxymethyl, 2-hydroxyeth-1-yl, 2-hydroxyprop-1-yl, 3-hydroxy-prop-1-yl, 1-hydroxyprop-2-yl, 2-hydroxybut-1-yl, 3-hydroxybut-1-yl, 4-hydroxybut-1-yl, 1-hydroxybut-2-yl, 1-hydroxybut-3-yl, 2-hydroxybut-3-yl, 1-hydroxy-2-methylprop-3-yl, 2-hydroxy-2-methylprop-3-yl or 2-hydroxymethylprop-2-yl, in particular 2-hydroxyethyl.

In the case of alkoxy-substituted alkyl, the alkyl group has in particular one alkoxy substituent. These radicals are referred to, depending on the number of carbon atoms, also as $C_n$-$C_m$-alkoxy-$C_n$-$C_m$-alkyl and are, for example, methoxymethyl, ethoxymethyl, 2-methoxy-ethyl, 1-methoxyethyl, 2-ethoxyethyl, 1-ethoxyethyl, n-propoxymethyl, isopropoxymethyl, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)-propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)/propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)-butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy) butyl, 4-(1-methylpropoxy)butyl, 4-(2-methylpropoxy)butyl or 4-(1,1-dimethylethoxy)butyl, preferably methoxymethyl, ethoxymethyl, 2-methoxyethyl, 2-ethoxyethyl, 2-(methoxy) propyl, 2-(ethoxy)propyl or 3-(methoxy)propyl, 3-(ethoxy) propyl.

Cycloalkyl is in particular $C_3$-$C_6$-cycloalkyl such as cyclopropyl, cyclobutyl, cyclopentyl and cyclohexyl.

The term "alkylene" includes in principle straight-chain or branched radicals preferably having 3 to 10 and particularly preferably having 3 to 8 carbon atoms, such as prop-1,2-ylene, prop-1,3-ylene, but-1,2-ylene, but-1,3-ylene, but-1,4-ylene, 2-methylprop-1,3-ylene, pent-1,2-ylene, pent-1,3-ylene, pent-1,4-ylene, pent-1,5-ylene, pent-2,3-ylene, pent-2,4-ylene, 1-methylbut-1,4-ylene, 2-methylbut-1,4-ylene, hex-1,3-ylene, hex-2,4-ylene, hex-1,4-ylene, hex-1,5-ylene, hex-1,6-ylene and the like. $C_0$-Alkylene is a single bond, $C_1$-alkylene is methylene and $C_2$-alkylene is 1,1-ethylene or 1,2-ethylene.

"5- or 6-membered aromatic heterocyclic radicals" having 1, 2, 3 or 4 heteroatoms which are selected from O, S and N include in particular heterocycles having 1, 2, 3 or 4 nitrogen atoms, heterocycles having 1 oxygen or 1 sulfur atom, heterocycles having 1 oxygen and 1 or 2 nitrogen atoms, and heterocycles having 1 sulfur atom and 1 or 2 nitrogen atoms. These include especially pyridinyl, pyrimidinyl, pyrazinyl, pyridazinyl, triazinyl, imidazolyl, pyrrolyl, pyrazolyl, thienyl, furanyl, oxazolyl, thiazolyl, isoxazolyl, tetrazolyl, thiadiazolyl and triazolyl. These may have 1, 2 or 3 of the substituents mentioned for $R^1$ on the nitrogen atoms and on the carbon atoms. If one of the substituents is hydroxyl, the radicals may also exist in a tautomeric form having a carbonyl group. Examples of 5- or 6-membered heterocyclic radicals having a fused carbocycle or being fused thereto include benzofuranyl, benzthienyl, indolyl, benzothiazolyl, benzoxazolyl, benzimidazolyl, benzopyrazolyl, quinolinyl, isoquinolinyl, quinoxalinyl, quinazolinyl, cinnolinyl, and corresponding partially hydrogenated groups.

Examples of phenyl having a fused carbocycle are in particular naphthyl, 5,6,7,8-tetrahydronapht-(1,2,3 or 4)-yl, indanyl and indenyl.

In connection with group A, the two binding sites of the alkylene chain are preferably located not on the same atom but form, where appropriate with the at least one group Z, a chain which has at least three and preferably at least four members and which separates the triazole ring from the nitrogen atom of the (partially) saturated nitrogen heterocycle, preferably by at least 5 bonds from one another. If A has no group Z, then A includes 4 to 10 carbon atoms, in particular 4 to 8 carbon atoms. The chain between the triazole ring and group B then has at least four carbon atoms. If A has at least one of said groups Z, then A includes 3 to 10 carbon atoms, in particular 3 to 8 carbon atoms. It is additionally possible for the saturated bonds in alkylene to be replaced by unsaturated bonds (alkenylene; alkynylene). This may result in straight-chain or branched unsaturated radicals whose number and arrangement of the carbon atoms corresponds to that of the aforementioned alkylene radicals, but where one or more single bonds are replaced by corresponding unsaturated double or triple bonds. In addition, alkylene may have a $C_3$-$C_6$-cycloalkanediyl group, e.g. cis- or trans-cyclopropane-1,2-diyl, cis- or trans-cyclobutane-1,2-diyl, cis- or trans-cyclopentane-1,2-diyl, cis- or trans-cyclopentane-1,3-diyl, cis- or trans-cyclohexane-1,2-diyl, cis- or trans-cyclohexane-1,3-diyl, cis- or trans-cyclohexane-1,4-diyl.

If the alkylene group in A includes at least one of the Z groups, this can be disposed in the alkylene chain at any point or preferably in position 1 or 2 of group A (viewed from the triazole ring). In particular, Z is located in position 1, i.e. Z is bonded to the triazole ring. The radicals COO and CONR$^5$ are in this case preferably disposed so that the carbonyl group is bonded to the triazole ring.

With a view to the use of the inventive compounds as dopamine $D_3$ receptor ligands, the variables A, B, $R^1$, $R^2$, $R^3$ and $R^4$ preferably have independently of one another the meanings indicated below:

A is $C_4$-$C_{10}$-alkylene or Z-$C_3$-$C_{10}$-alkylene, where Z is bonded to the triazole ring, and alkylene may have a double bond. Z has herein the aforementioned meanings and is selected in particular from O, S, COO, NR$^5$ and CO and specifically from O and S. A preferably separates the triazole ring from the nitrogen atom of the (partially) saturated nitrogen heterocycle by at least 5 bonds or 4 chain members. A is, in particular, Z-CH$_2$CH$_2$CH$_2$, Z-CH$_2$CH$_2$CH$_2$CH$_2$, Z-CH$_2$CH=CHCH$_2$, Z-CH$_2$C(CH$_3$)=CHCH$_2$, Z-CH$_2$C(=CH$_2$)CH$_2$, Z-CH$_2$CH(CH$_3$)CH$_2$, (CH$_2$)$_4$, (CH$_2$)$_5$, CH$_2$CH$_2$CH=CHCH$_2$, CH$_2$CH$_2$C(CH$_3$)=CHCH$_2$, CH$_2$CH$_2$C(=CH$_2$)CH$_2$ or CH$_2$CH$_2$CH(CH$_3$)CH$_2$. In particularly preferred compounds of the formula I, A is S—$C_3$-$C_{10}$-alkylene.

B is CH$_2$CH$_2$.

$R^1$ in a preferred embodiment of the invention is phenyl which is unsubstituted or has one or two substituents which are selected independently of one another from $C_1$-$C_6$-alkyl, OR$^9$, $C_1$-$C_6$-alkoxy, $C_1$-$C_4$-fluoroalkyl, phenyl, CN and halogen and/or may be fused to a 6-membered aromatic carbocycle, in particular is unsubstituted phenyl or 4-fluoro-phenyl. In another preferred embodiment, $R^1$ is a 5- or 6-membered preferred embodiment $R^1$ is a 5- or 6-membered heteroaromatic radical (=hetaryl) which may have 1, 2 or 3 heteroatoms selected from N, O and S and which may have a fused benzene ring. The heteroaromatic radical may be substituted in the abovementioned manner. Preferred substituents on $R^1$ are CN, $C_1$-$C_4$-alkyl, OR$^9$, halogen, $C_1$-$C_4$-fluoroalkyl, and phenyl, in particular CN, CH$_3$, OH, OCH$_3$, CHF$_2$, CF$_3$, halogen, phenyl and tert-butyl. In particular, $R^1$ is unsubstituted or has one or two of the substituents previously mentioned as preferred, e.g. a methyl group, one or two methoxy groups. In particular, $R^1$ is optionally substituted pyrrolyl, thienyl, furanyl, tetrazolyl, benzothienyl, indolyl, benzothiazolyl, pyridyl or pyrazinyl, particularly preferably is optionally substituted 2- or 3-pyrrolyl or optionally substituted 2- or 3-thienyl. Preferred among these are compounds I in which $R^1$ is pyrrol-2-yl, 1-($C_1$-$C_4$-alkyl)pyrrol-2-yl, 1-($C_1$-$C_4$-alkyl)pyrrol-3-yl, 2-thienyl, 3-thienyl, benzothien-2-yl, benzothiazol-2-yl, 2-furyl, 3-furyl, 2-pyridinyl, 3-pyridinyl, 4-pyridinyl or 2-pyrazinyl, in particular is 1-($C_1$-$C_4$-alkyl) pyrrol-2-yl, 1-($C_1$-$C_4$-alkyl)pyrrol-3-yl, 2-thienyl or 3-thienyl. In a particularly preferred embodiment, $R^1$ is pyrrolyl, in particular 2-pyrrolyl, which is unsubstituted or preferably has 1 or 2 substituents selected from $C_1$-$C_4$-alkyl and $C_3$-$C_6$-cycloalkyl, with in particular one substituent being disposed on the nitrogen. Particularly preferred among these are compounds I with $R^1$=1-methylpyrrol-2-yl. In another particularly preferred embodiment, $R^1$ is phenyl which optionally has one of the aforementioned groups and in particular a halogen atom as substituent. In this embodiment, $R^1$ is in particular phenyl or p-fluorophenyl.

$R^2$ is preferably hydrogen.

$R^3$ is $C_2$-$C_{10}$-alkyl, in particular $C_2$-$C_6$-alkyl, $C_3$-$C_6$-cycloalkyl, benzyl or phenyl, where benzyl or phenyl may be unsubstituted or substituted in the aforementioned manner on the phenyl ring, e.g. have one or two substituents which are selected independently of one another from $C_1$-$C_6$-alkyl, $C_1$-$C_6$-alkoxy, halogen, CN, $NO_2$, $CF_3$, $CHF_2$ or halogen. $R^3$ is particularly preferably $C_2$-$C_4$-alkyl, in particular ethyl, n-propyl, isopropyl, n-butyl, 2-butyl, tert-butyl, also cyclopropyl, cyclobutyl, cyclopentyl, cyclohexyl or phenyl which is unsubstituted or may be substituted once or twice by $C_1$-$C_4$-alkyl, $C_1$-$C_4$-alkoxy, $CF_3$, $CHF_2$ or halogen. If $R^1$ is optionally substituted hetaryl, then compounds in which $R^3$ is methyl are also preferred. $R^3$ is very particularly preferably $C_2$-$C_4$-alkyl.

$R^4$ is preferably different from hydrogen and is in particular $C_1$-$C_4$-alkyl and $C_3$-$C_6$-cycloalkyl, particularly preferably $C_1$-$C_4$-alkyl and specifically methyl.

With a view to their use, particularly preferred compounds of the formula I are those in which the variables A, B, $R^1$, $R^2$, $R^3$ and $R^4$ together have the meanings indicated as preferred.

In addition, compounds preferred among the compound of the formula I are those in which the group —C(O)$R^3$ is disposed in the 3 position (meta position) to the binding site of B. If B is $CH_2CH_2$, this is the 7 position of the 1,2,3,4-tetrahydroisoquinoline unit. If B is $CH_2$, this is the 6 position of the 1,3-dihydro-isoindole unit.

$R^5$ in $NR^5$ groups is preferably H, $C_1$-$C_4$-alkyl, phenyl-substituted $C_1$-$C_4$-alkyl or $COR^{11}$. $NR^5$ is particularly preferably NH, $NCH_3$, $NCOCH_3$ or $NCH_2$-phenyl.

$R^6$ in $OR^6$ substituents is preferably H, $C_1$-$C_4$-alkyl, $CF_3$, $CHF_2$ or phenyl. $OR^6$ is particularly preferably methoxy, trifluoromethoxy or phenoxy.

$R^6$ in $COOR^6$ substituents is H or $C_1$-$C_4$-alkyl. $COOR^6$ is particularly preferably $C_1$-$C_4$-alkoxycarbonyl such as methoxycarbonyl, ethoxycarbonyl, n-propoxycarbonyl, i-propoxycarbonyl, n-butoxycarbonyl or t-butoxy-carbonyl.

$R^7$ in $CONR^7R^8$ substituents is preferably H or $C_1$-$C_4$-alkyl and $R^8$ is preferably H, $C_1$-$C_4$-alkyl or $COR^{11}$. $CONR^7R^8$ is particularly preferably $CONH_2$, $CONHCH_3$, $CON(CH_3)_2$ or $CONHCOCH_3$.

$R^7$ in $NR^7R^8$ substituents is preferably H, $C_1$-$C_4$-alkyl or phenyl-substituted $C_1$-$C_4$-alkyl and $R^8$ is H, $C_1$-$C_4$-alkyl or $COR^{11}$. $NR^7R^8$ is particularly preferably $NH_2$, $NHCH_3$, $N(CH_3)_2$, NH-benzyl or $NHCOCH_3$.

$R^7$ in $SO_2NR^7R^8$ substituents is preferably H or $C_1$-$C_4$-alkyl and $R^8$ is preferably H, $C_1$-$C_4$-alkyl or $COR^{11}$. $SO_2NR^7R^8$ is particularly preferably sulfamoyl.

$R^9$ in $SR^9$ substituents is preferably alkyl. $SR^9$ is particularly preferably thiomethyl.

$R^9$ in $SO_2R^9$ substituents is preferably H or $C_1$-$C_4$-alkyl. $SO_2R^9$ is particularly preferably methylsulfonyl.

$R^{10}$ in $COR^{10}$ substituents is preferably H, $C_1$-$C_4$-alkyl or phenyl. $COR^{10}$ is particularly preferably formyl, acetyl or benzoyl.

$R^{11}$ in $COR^{11}$ substituents is preferably H, $C_1$-$C_4$-alkyl or Phenyl. $COR^{11}$ is particularly preferably formyl, acetyl or benzoyl.

In a preferred embodiment of the invention are the compounds of the general formula Ia,

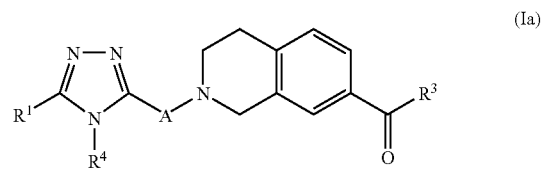

(Ia)

in which A, $R^1$ $R^3$ and $R^4$ have the meanings indicated above, i.e. compounds of the general formula I as defined above in which B is a $CH_2$—$CH_2$ unit, $R^2$ is hydrogen, and the radical C(O)$R^3$ is disposed in the 7 position. That stated above applies to the preferred meanings of $R^1$, $R^3$, $R^4$ and A.

In particular, A is $C_4$-$C_{10}$-alkylene or Z-$C_3$-$C_{10}$-alkylene, where Z is bonded to the triazole ring, and alkylene may have a double bond. Z herein has the aforementioned meanings and is in particular selected from O, S, COO, $NR^5$ and CO and specifically from O and S. A preferably separates the triazole ring from the nitrogen atom of the (partially) saturated nitrogen heterocycle by at least 5 bonds or 4 chain members. In particular, A is Z-$CH_2CH_2CH_2$, Z-$CH_2CH_2CH_2CH_2$, Z-$CH_2CH$=$CHCH_2$, Z-$CH_2C(CH_3)$=$CHCH_2$, Z-$CH_2C$(=$CH_2$)$CH_2$, Z-$CH_2CH(CH_3)CH_2$, $(CH_2)_4$, $(CH_2)_5$, $CH_2CH_2CH$=$CHCH_2$, $CH_2CH_2C(CH_3)$=$CHCH_2$, $CH_2CH_2C$(=$CH_2$)$CH_2$ or $CH_2CH_2CH(CH_3)CH_2$. A in particularly preferred compounds of the formula I is S—$C_3$-$C_{10}$-alkylene.

$R^1$ in formula Ia is in particular optionally substituted phenyl, pyrrolyl, thienyl, furanyl, tetrazolyl, benzothienyl, indolyl, benzothiazolyl, pyridyl and pyrazinyl, particularly preferably is optionally substituted 2- or 3-pyrrolyl or optionally substituted 2- or 3-thienyl. Preferred among these are compounds I in which $R^1$ is pyrrol-2-yl, 1-($C_1$-$C_4$-alkyl)pyrrol-2-yl, 1-($C_1$-$C_4$-alkyl)pyrrol-3-yl, 2-thienyl, 3-thienyl, benzothien-2-yl, benzothiazol-2-yl, 2-furyl, 3-furyl, 2-pyridinyl, 3-pyridinyl, 4-pyridinyl or 2-pyrazinyl in particular is 1-($C_1$-$C_4$-alkyl)pyrrol-2-yl, 1-($C_1$-$C_4$-alkyl)pyrrol-3-yl, 2-thienyl or 3-thienyl. In a particularly preferred embodiment, $R^1$ is pyrrolyl, in particular 2-pyrrolyl, which is unsubstituted or preferably has 1 or 2 substituents selected from $C_1$-$C_4$-alkyl and $C_3$-$C_6$-cycloalkyl, with one substituent in particular being disposed on the nitrogen. Particularly preferred among these are compounds I with $R^1$=1-methylpyrrol-2-yl. In another particularly preferred embodiment, $R^1$ is phenyl which optionally has one of the aforementioned groups and in particular a halogen atom as substituent. In this embodiment, $R^1$ is in particular phenyl or p-fluorophenyl.

$R^3$ in formula Ia is in particular $C_2$-$C_6$-alkyl, $C_3$-$C_6$-cycloalkyl, benzyl or phenyl, where benzyl or phenyl may be unsubstituted or substituted in the aforementioned manner on the phenyl ring, e.g. have one or two substituents which are selected independently of one another from $C_1$-$C_6$-alkyl, $C_1$-$C_6$-alkoxy, halogen, CN, $NO_2$, $CF_3$, $CHF_2$ or halogen. $R^3$ is particularly preferably $C_2$-$C_4$-alkyl, in particular ethyl, n-propyl, isopropyl, n-butyl, 2-butyl, tert-butyl, also cyclopropyl, cyclobutyl, cyclopentyl, cyclohexyl or phenyl which is unsubstituted or may be substituted once or twice by $C_1$-$C_4$-alkyl, $C_1$-$C_4$-alkoxy, $CF_3$, $CHF_2$ or halogen. If $R^1$ is optionally substituted hetaryl, then preferred compounds are also those in which $R^3$ is methyl. $R^3$ is very particularly preferably $C_2$-$C_4$-alkyl.

$R^4$ in formula Ia is preferably a radical different from hydrogen and in particular is $C_1$-$C_4$-alkyl and $C_3$-$C_6$-cycloalkyl, in particular $C_1$-$C_4$-alkyl and specifically methyl.

Preferred compounds of the formula Ia are in particular compounds of the formula Ia'

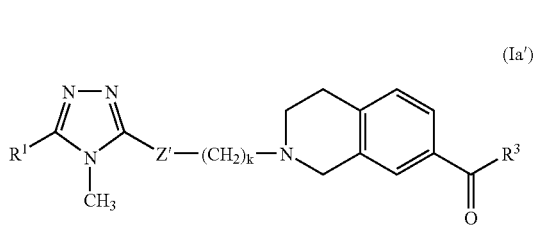

in which $R^1$ and $R^3$ have the meanings indicated above, especially the meanings indicated as preferred, k is 3 or 4 and Z' is O, $CH_2$ or, in particular, S.

Among these, particularly preferred compounds of the formula Ia' are those in which $R^1$ and $R^3$ have, alone or particularly preferably in combination, the following meanings:

$R^1$ phenyl, 4-fluorophenyl, pyrrol-2-yl, 1-methylpyrrol-2-yl, 2-thienyl, 3-thienyl, benzothien-2-yl, 2-furyl, 3-furyl, benzothiazol-2-yl, 2-pyridinyl, 3-pyridinyl, 4-pyridinyl or 2-pyrazinyl. $R^1$ is in particular 1-methylpyrrol-2-yl;

$R^3$ $C_2$-$C_4$-alkyl or phenyl which is unsubstituted or may be substituted once or twice by $C_1$-$C_4$-alkyl, $C_1$-$C_4$-alkoxy, $CF_3$, $CHF_2$ or halogen, or if $R^1$ is different from phenyl may also be methyl. $R^3$ is in particular $C_2$-$C_4$-alkyl.

Examples of particularly preferred compounds I are compounds of the formula Ia' which are listed in Table 1 below and in which $R^1$, $R^3$, k and Z' in formula Ia' have the meaning indicated in one line of Table 1 in each case. (Compounds Ia'-1 to Ia'-92).

TABLE 1

| Compound Ia' No. | $R^1$ | Z' | k | $R^3$ |
|---|---|---|---|---|
| 1 | 4-Pyridyl | S | 3 | Phenyl |
| 2 | 3-Thienyl | S | 3 | tert-Butyl |
| 3 | 2-Furyl | S | 3 | Phenyl |
| 4 | 1-Methylpyrrol-2-yl | S | 3 | Methyl |
| 5 | 2-Thienyl | S | 3 | Ethyl |
| 6 | 3-Thienyl | S | 3 | Methyl |
| 7 | Phenyl | S | 3 | Cyclohexyl |
| 8 | 3-Pyridyl | S | 3 | Cyclopropyl |
| 9 | 4-Pyridyl | S | 3 | Ethyl |
| 10 | 3-Pyridyl | S | 3 | tert-Butyl |
| 11 | 4-Pyridyl | S | 3 | Cyclohexyl |
| 12 | 1-Methylpyrrol-2-yl | S | 3 | Phenyl |
| 13 | Phenyl | O | 3 | Phenyl |
| 14 | 3-Thienyl | S | 3 | Cyclopropyl |
| 15 | 1-Methylpyrrol-2-yl | S | 3 | Ethyl |
| 16 | 2-Furyl | S | 3 | Cyclohexyl |
| 17 | Phenyl | $CH_2$ | 3 | Phenyl |
| 18 | 3-Thienyl | S | 3 | Phenyl |
| 19 | Phenyl | S | 3 | Phenyl |
| 20 | 3-Thienyl | S | 3 | Ethyl |
| 21 | Phenyl | $CH_2$ | 3 | Ethyl |
| 22 | 2-Pyrazinyl | S | 3 | Cyclopropyl |
| 23 | 1-Methylpyrrol-2-yl | S | 3 | Cyclopropyl |
| 24 | 3-Thienyl | S | 3 | Cyclohexyl |
| 25 | Phenyl | S | 3 | Ethyl |
| 26 | 2-Pyrazinyl | S | 3 | Ethyl |
| 27 | 1-Methylpyrrol-2-yl | O | 3 | Ethyl |
| 28 | 2-Pyrazinyl | S | 3 | Methyl |
| 29 | 4-Pyridyl | S | 3 | tert-Butyl |
| 30 | 2-Furyl | S | 3 | Methyl |
| 31 | 1-Methylpyrrol-2-yl | S | 3 | tert-Butyl |
| 32 | 2-Furyl | S | 3 | Ethyl |
| 33 | 4-Pyridyl | S | 3 | Methyl |
| 34 | Phenyl | S | 3 | Cyclopropyl |
| 35 | Phenyl | S | 3 | tert-Butyl |
| 36 | 2-Thienyl | S | 3 | Methyl |

TABLE 1-continued

| Compound Ia' No. | $R^1$ | Z' | k | $R^3$ |
|---|---|---|---|---|
| 37 | 2-Pyrazinyl | S | 3 | Phenyl |
| 38 | 2-Thienyl | S | 3 | Phenyl |
| 39 | 3-Pyridyl | S | 3 | Methyl |
| 40 | 1-Methylpyrrol-2-yl | $CH_2$ | 3 | Ethyl |
| 41 | 3-Pyridyl | S | 3 | Ethyl |
| 42 | 2-Thienyl | S | 3 | Cyclohexyl |
| 43 | 2-Furyl | S | 3 | Cyclopropyl |
| 44 | 2-Pyrazinyl | S | 3 | Cyclohexyl |
| 45 | 4-Pyridyl | S | 3 | Cyclopropyl |
| 46 | 3-Pyridyl | S | 3 | Phenyl |
| 47 | 1-Methylpyrrol-2-yl | S | 4 | Ethyl |
| 48 | 2-Thienyl | S | 3 | Cyclopropyl |
| 49 | Phenyl | O | 3 | Ethyl |
| 50 | 2-Pyrazinyl | S | 3 | tert-Butyl |
| 51 | 3-Pyridyl | S | 3 | Cyclohexyl |
| 52 | 2-Thienyl | S | 3 | tert-Butyl |
| 53 | 1-Methylpyrrol-2-yl | S | 3 | Cyclohexyl |
| 54 | 2-Furyl | S | 3 | tert-Butyl |
| 55 | 2-Thienyl | S | 3 | 3-Fluorophenyl |
| 56 | Phenyl | S | 4 | 3-Fluorophenyl |
| 57 | Benzo [b] thien-2-yl | S | 3 | Ethyl |
| 58 | 2-Pyrazinyl | S | 3 | 3-Fluorophenyl |
| 59 | 1H-Pyrrol-2-yl | S | 3 | tert-Butyl |
| 60 | 1-Methylpyrrol-2-yl | S | 3 | 3-Fluorophenyl |
| 61 | Benzo [b] thiazol-2-yl | S | 3 | Phenyl |
| 62 | 2-Furyl | S | 3 | 3-Fluorophenyl |
| 63 | 3-Pyridyl | S | 3 | 3-Fluorophenyl |
| 64 | 1H-Pyrrol-2-yl | S | 3 | Phenyl |
| 65 | 1H-Pyrrol-2-yl | S | 3 | Ethyl |
| 66 | 3-Thienyl | S | 3 | 3-Fluorophenyl |
| 67 | Phenyl | S | 4 | Phenyl |
| 68 | Phenyl | S | 3 | 3-Fluorophenyl |
| 69 | 1-Methylpyrrol-2-yl | S | 3 | 3-Fluorophenyl |
| 70 | Benzo [b] thiazol-2-yl | S | 3 | Ethyl |
| 71 | Pyridin-2-yl | S | 3 | Ethyl |
| 72 | 1-Methylpyrrol-2-yl | S | 4 | 3-Fluorophenyl |
| 73 | 1H-Pyrrol-2-yl | S | 3 | Cyclopropyl |
| 74 | 1H-Pyrrol-2-yl | S | 3 | Cylcohexyl |
| 75 | Benzo [b] thien-2-yl | S | 3 | Phenyl |
| 76 | 3-Pyridyl | S | 3 | Ethyl |
| 77 | Benzo [b] thiazol-2-yl | S | 3 | 3-Fluorophenyl |
| 78 | 2-Furyl | S | 4 | Cyclopropyl |
| 79 | 2-Thienyl | S | 4 | Cyclohexyl |
| 80 | Benzo [b] thien-2-yl | S | 3 | Cyclopropyl |
| 81 | 4-F-Phenyl | S | 3 | Ethyl |
| 82 | 4-F-Phenyl | $CH_2$ | 3 | Ethyl |
| 83 | 2-Thienyl | S | 3 | 4-Fluorophenyl |
| 84 | Phenyl | S | 4 | 4-Fluorophenyl |
| 85 | 2-Pyrazinyl | S | 3 | 4-Fluorophenyl |
| 86 | 1-Methylpyrrol-2-yl | S | 3 | 4-Fluorophenyl |
| 87 | 3-Pyridyl | S | 3 | 4-Fluorophenyl |
| 88 | 3-Thienyl | S | 3 | 4-Fluorophenyl |
| 89 | Phenyl | S | 3 | 4-Fluorophenyl |
| 90 | 1-Methylpyrrol-2-yl | S | 3 | 4-Fluorophenyl |
| 91 | 1-Methylpyrrol-2-yl | S | 4 | 4-Fluorophenyl |
| 92 | Benzo [b] thiazol-2-yl | S | 3 | 4-Fluorophenyl |

Another preferred embodiment of the invention are the compounds of the general formula Ib

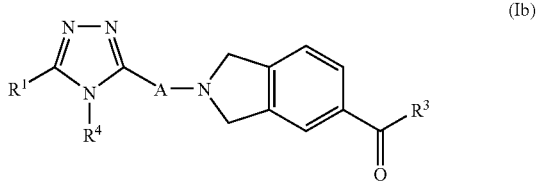

in which A, $R^1$ $R^3$ and $R^4$ have the meanings indicated above, i.e. compounds of the general formula I as defined above in which B is a CH$_2$ unit, R$^2$ is hydrogen, and the radical C(O)R$^3$ is disposed in the 6 position. That stated above for formula Ia applies to the preferred meanings of R$^1$, R$^3$, R$^4$ and A.

Particularly preferred compounds of the formula Ib are compounds of the formula Ib'

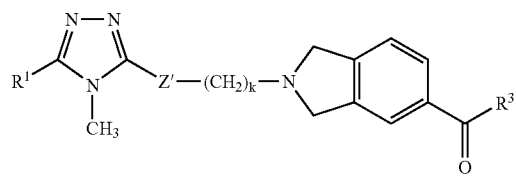
(Ib')

in which R$^1$ and R$^3$ have the meanings indicated above, especially the meanings indicated as preferred, k is 3 or 4 and Z' is O, CH$_2$ or, in particular, S.

Of these, particularly preferred compounds of the formula Ib' are those in which R$^1$ and R$^3$ have, alone or particularly preferably in combination, the following meanings:

R$^1$ phenyl, 4-fluorophenyl, pyrrol-2-yl, 1-methylpyrrol-2-yl, 2-thienyl, 3-thienyl, benzothien-2-yl, 2-furyl, 3-furyl, benzothiazol-2-yl, 2-pyridinyl, 3-pyridinyl, 4-pyridinyl or 2-pyrazinyl. R$^1$ is in particular 1-methylpyrrol-2-yl;

R$^3$ C$_2$-C$_4$-alkyl or phenyl which is unsubstituted or may be substituted once or twice by C$_1$-C$_4$-alkyl, C$_1$-C$_4$-alkoxy, CF$_3$, CHF$_2$ or halogen, or if R$^1$ is different from phenyl may also be methyl. R$^3$ is in particular C$_2$-C$_4$-alkyl.

Examples of particularly preferred compounds Ib are compounds of the formula Ib' in which R$^1$, R$^3$, k and Z' in formula Ib' have the meaning indicated in one line of Table 1 in each case. (Compounds Ib'-1 to 1b'-92).

The inventive compounds are prepared in analogy to methods which are known from the literature and are described for preparing triazole compounds of this type, e.g. in WO 00/42036. This ordinarily entails a) reacting a compound of the general formula (II)

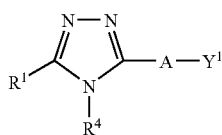
(II)

in which y$^1$ is a usual leaving group such as, for example, halogen, alkylsulfonyloxy, arylsulfonyloxy, trifluoromethylsulfonyloxy or the like, with a compound of the general formula (III)

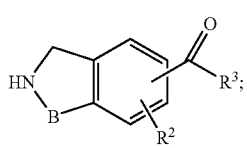
(III)

or b) reacting a compound of the general formula (IV)

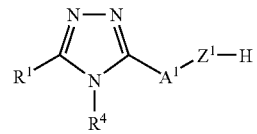
(IV)

in which Z$^1$ is O, S or NR$^5$ and A$^1$ is a bond or is C$_1$-C$_{10}$-alkylene, with a compound of the general formula (V)

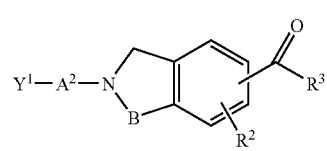
(V)

where Y$^1$ has the meaning indicated above, and A$^2$ is C$_2$-C$_{10}$-alkylene, where A$^1$ and A$^2$ together have 3 to 10 C atoms, and A$^1$ and/or A$^2$ optionally include at least one group Z; or c) reacting a compound of the general formula (VI)

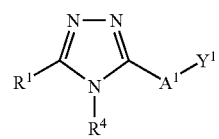
(VI)

in which Y$^1$ and A$^1$ have the meanings indicated above, with a compound of the general formula (VII)

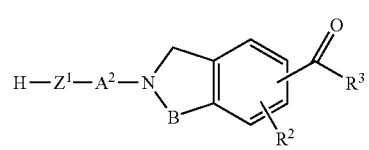
(VII)

in which Z$^1$ and A$^2$ have the meanings indicated above; or d) umpolung of an aldehyde of the general formula (VIII)

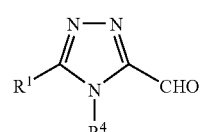
(VIII)

using reagents known from the literature, such as, for example, 1,3-propanedithiol, KCN/water, TMSCN (trimethylsilyl cyanide) or KCN/morpholine as described, for example, in Albright *Tetrahedron,* 1983, 39, 3207 or D. Seebach *Synthesis* 1969, 17 and 1979, 19 or H. Stetter *Angew. Chem. Int. Ed.* 1976, 15, 639 or van Niel et al. *Tetrahedron* 1989, 45, 7643 Martin et al. *Synthesis* 1979, 633, to give the products (VIIIa) (by way of example with 1,3-propanedithiol)

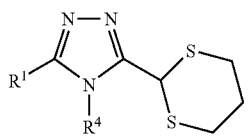
(VIIIa)

and subsequent chain extension with compounds of the general formula (IX)

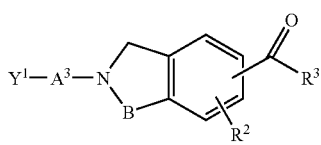
(IX)

where $Y^1$ has the meaning indicated above, and $A^3$ is $C_3$-$C_9$-alkylene which may comprise a group Z. The carbonyl function in the group —C(O)—$R^3$ in formula IX is present where appropriate in protected form. After deprotection or reduction, compounds of the formula (I-1)

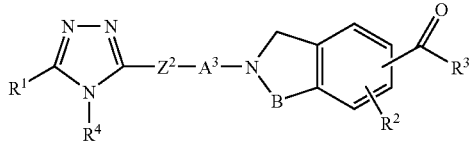
(I-1)

in which $Z^2$ is CO or a methylene group, and $Z^2$ and $A^3$ together have 4 to 10 C atoms, are obtained in this way. It is alternatively possible e) to react an aldehyde of the general formula (VIII) with a compound of the general formula (X)

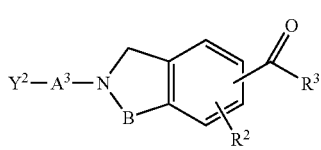
(X)

in which $Y^2$ is a phosphorane or a phosphonic ester, and $A^3$ has the meaning indicated above, in analogy to usual methods as described for example in Houben Weyl "*Handbuch der Organischen Chemie*" 4th edition, Thieme Verlag Stuttgart, Volume V/1b page 383 et seq. or Vol. V/1c page 575 et seq., or f) to react a compound of the general formula (XI)

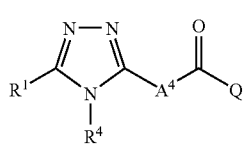
(XI)

in which $A^4$ is $C_3$-$C_9$-alkylene or $C_2$-$C_9$-alkylene which includes a group Z as defined above, Q is H or OH, with a compound of the formula IIIa under reductive conditions. The reaction takes place in analogy to methods known from the literature, as described for example in *J. Org. Chem.* 1986, 50, 1927 or WO 92/20655.

The process for preparing a compound of the formula I in which A includes the group COO comprises reacting a compound of the general formula XII

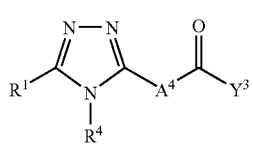
(XII)

in which $y^3$ is OH, $OC_1$-$C_4$-alkyl, Cl or together with CO is an activated carboxyl group (activated ester group), and $A^4$ is $C_0$-$C_9$-alkylene, with a compound of the formula XIII

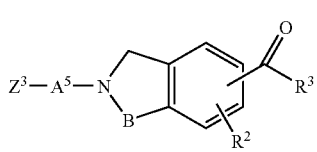
(XIII)

in which $Z^3$ is OH, and $A^5$ is $C_2$-$C_6$-alkylene, where $A^5$ and $A^4$ together have 3 to 10 C atoms. Compounds I with 2=$CONR^5$ can be prepared in an analogous manner by reacting XII with XIII in which $Z^3$ is $NHR^5$.

Compounds of the general formula III are disclosed in the literature or can be prepared by introducing a group —C(O)—$R^3$ into a compound of the general formula XIV,

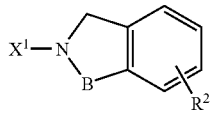
(XIV)

in which $X^1$ is hydrogen or preferably an NH protective group, in a manner known per se, e.g. by acylating the compound XIV under Friedel-Crafts conditions, resulting in a compound of the formula IIIa

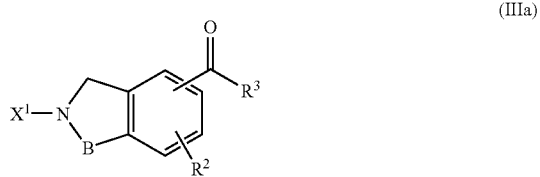

(IIIa)

and removing the protective group $X^1$ where appropriate. Suitable NH protective groups, their introduction and their removal are described for example from Kocienski, "Protecting Groups" Georg Thieme-Verlag, Stuttgart, New-York, 2000, pages 185-216, and include in particular trifluoromethylcarbonyl, methoxy- and ethoxycarbonyl, Boc, Z, Zbz, Aloc, Fmoc, Teoc and Troc groups.

Suitable methods for Friedel-Crafts acylation of compounds XIV are described for example in G. L. Grunewald et al, J. Med. Chem. 42 (1999), pages 118-134, F. E. Ali et al., J. Med. Chem. 25 (1982), pages 1235-1240.

Compounds of the formula III or IIIa can additionally be prepared by cyclization of compounds of the general formula XV

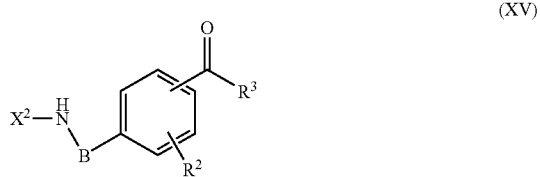

(XV)

in which $X^2$ is an alkylcarbonyl group, e.g. acetyl, with formaldehyde or a formaldehyde equivalent such as formalin solution, trioxane, paraformaldehyde and the like with acid catalysis in analogy to the process described in A. B. Venkov et al., Synth. Commun. 25 (1995), pages 1419-1425.

The compounds of the formulae V, VII, IX, X and XIII can be prepared from the compounds of the formula III or IIIa in analogy to the patent literature cited at the outset, e.g. by the processes of WO 00/42036.

$R^1$, $R^2$, $R^3$, $R^4$, A, and B and X in the above formulae II to XV have the meanings indicated in connection with the formulae I, Ia and Ia'.

Compounds of the general formula XIV are disclosed in the literature or can be prepared by the methods described in P. L. Julian, J. Am. Chem. Soc. 70 (1948) pages 180-183, G. E. Hein, J. Am. Chem. Soc. 84 (1962), pages 4487-4494 and WO 00/21905.

The triazole compounds of the formulae II, IV, VI, VIII, VIIIa, XI and XII are either known or can be prepared by known processes as described for example in A. R. Katritzky, C. W. Rees (ed.) "Comprehensive Heterocyclic Chemistry", Pergamon Press, or "The Chemistry of Heterocyclic Compounds" J. Wiley & Sons Inc. NY and the literature cited therein, or in S. Kubota et al. Chem. Pharm. Bull 1975, 23, 955, WO 99/02503 or Vosilevskii et al. Izv. Akad. Nauk. SSSR Ser. Khim 1975, 23, 955; Rappoport et al. J. Org. Chem. 37 (1972), page 3618.

The inventive compounds and the starting materials and the intermediates can also be prepared in analogy to the methods described in the patent publications mentioned at the outset.

The reactions described above generally take place in a solvent at temperatures between room temperature and the boiling point of the solvent used. Examples of solvents which can be used are esters such as ethyl acetate, ethers such as diethyl ether or tetra-hydrofuran, dimethylformamide, dimethyl sulfoxide, dimethoxyethane, toluene, xylene, acetonitrile, ketones such as acetone or methyl ethyl ketone, or alcohols such as ethanol or butanol.

An acid-binding agent is present if desired. Suitable acid-binding agents are inorganic bases such as sodium or potassium carbonate, sodium or potassium bicarbonate, sodium methoxide, sodium ethoxide, sodium hydride or organometallic compounds such as butyl-lithium or alkylmagnesium compounds, or organic bases such as triethylamine or pyridine. The latter can serve simultaneously as solvents.

Process (f) takes place under reducing conditions, e.g. with use of sodium borohydride, sodium cyanoborohydride or triacetoxyborohydride, where appropriate in acid medium or in the presence of a Lewis acid such as, for example, zinc chloride or by means of catalytic hydrogenation.

The crude product is isolated in a conventional way, for example by filtration, removal of the solvent by distillation or extraction from the reaction mixture etc. The resulting compounds can be purified in a conventional way, for example by recrystallization from a solvent, chromatography or conversion into an acid addition compound.

The acid addition salts are prepared in a conventional way by mixing the free base with the appropriate acid, where appropriate in solution in an organic solvent, for example a low alcohol such as methanol, ethanol or propanol, an ether such as methyl t-butyl ether, a ketone such as acetone or methyl ethyl ketone or an ester such as ethyl acetate.

The inventive triazole compounds of the formula I are highly selective dopamine $D_3$ receptor ligands which, because of their low affinity for other receptors such as $D_1$ receptors, $D_4$ receptors, α1- and/or α2-adrenergic receptors, serotinergic receptors, muscarinergic receptors, histaminic receptors, opiate receptors and, in particular, for dopamine $D_2$ receptors, have fewer side effects than classical neuroleptics which comprise $D_2$ receptor antagonists.

The high affinity of the inventive compounds for $D_3$ receptors is reflected in very low in vitro $K_i$ values of ordinarily less than 100 nM (nmol/l) and especially of less than 50 nM. Binding affinities for $D_3$ receptors can for example be determined via the displacement of [$^{125}$I]-iodosulpride in receptor-binding studies.

Particularly important according to the invention are compounds whose selectivity $K_i(D_2)/K_i(D_3)$ is preferably at least 10, even better at least 30 and particularly advantageously at least 50. Receptor-binding studies on $D_1$, $D_2$ and $D_4$ receptors can be carried out for example via the displacement of [$^3$H] SCH23390, [$^{125}$I]iodosulpride and [$^{125}$I]spiperone.

The inventive compounds additionally have better bioavailability and better cerebral availability than comparable $D_3$ receptor ligands based on known triazole compounds having a tetrahydroisoquinoline or dihydro-isoindole residue and ought therefore to have the abovementioned advantages over comparable substances.

The compounds can, because of their binding profile, be used for the treatment of conditions which respond to dopamine $D_3$ ligands, i.e. they are effective for the treatment of those disorders or conditions where an influencing (modulation) of dopamine $D_3$ receptors leads to an improvement in the clinical condition or to cure of the disease. Examples of such conditions are disorders or conditions of the central nervous system.

Disorders or conditions of the central nervous system mean disorders affecting the spinal cord or, in particular, the brain. The term "disorder" in the sense according to the invention refers to abnormalities which are usually regarded as pathological states or functions and may reveal themselves in the form of particular signs, symptoms and/or dysfunctions. The inventive treatment may be directed at individual disorders, i.e. abnormalities or pathological states, but it is also possible for a plurality of abnormalities, which are causally connected together where appropriate, to be combined into patterns, i.e. syndromes, which can be treated according to the invention.

The disorders which can be treated according to the invention include in particular psychiatric and neurological disorders. These comprise in particular organic disorders, symptomatic disorders included, such as psychoses of the acute exogenous type or associated psychoses with an organic or exogenous cause, e.g. associated with metabolic disorders, infections and endocrinopathies; endogenous psychoses such as schizophrenia and schizotypal and delusional disorders; affective disorders such as depressions, mania and manic/depressive states; and combined forms of the disorders described above; neurotic and somatoform disorders, and disorders associated with stress; dissociative disorders, e.g. deficits, clouding and splitting of consciousness and personality disorders; disorders of attention and waking/sleeping behavior, such as behavioral disorders and emotional disorders starting in childhood and adolescence, e.g. hyperactivity in children, intellectual deficits, especially attention deficit disorders, disorders of memory and cognition, e.g. learning and memory impairment (impaired cognitive function), dementia, narcolepsy and sleeping disorders, e.g. restless legs syndrome; developmental disorders; anxiety states; delirium; disorders of the sex life, e.g. male impotence; eating disorders, e.g. anorexia or bulimia; addiction; and other undefined psychiatric disorders.

The disorders which can be treated according to the invention also include parkinsonism and epilepsy and, in particular, the affective disorders associated therewith.

Addictive disorders include the psychological disorders and behavioral disorders caused by the abuse of psychotropic substances such as pharmaceuticals or drugs, and other addictive disorders such as, for example, compulsive gambling (impulse control disorders not elsewhere classified). Examples of addictive substances are: opioids (e.g. morphine, heroin, codeine); cocaine; nicotine; alcohol; substances which interact with the GABA chloride channel complex, sedatives, hypnotics or tranquilizers, for example benzodiazepines; LSD; cannabinoids; psychomotor stimulants such as 3,4-methylenedioxy-N-methylamphetamine (Ecstasy); amphetamine and amphetamine-like substances such as methylphenidate or other stimulants, including caffeine. Addictive substances requiring particular attention are opioids, cocaine, amphetamine or amphetamine-like substances, nicotine and alcohol.

With a view to the treatment of addictive disorders, the inventive compounds of the formula I which are particularly preferred are those which themselves have no psychotropic effect. This can also be observed in a test on rats which reduce the self-administration of psychotropic substances, for example cocaine, after administration of compounds which can be used according to the invention.

According to a further aspect of the present invention, the inventive compounds are suitable for the treatment of disorders the causes of which can at least in part be attributed to an abnormal activity of dopamine $D_3$ receptors.

According to another aspect of the present invention, the treatment is directed in particular at those disorders which can be influenced by a binding of, preferably exogenously added, binding partners (ligands) to dopamine $D_3$ receptors in the sense of an expedient medical treatment.

The conditions which can be treated with the inventive compounds are frequently characterized by a progressive development, i.e. the states described above change over the course of time, the severity usually increasing and, where appropriate, states possibly interchanging or other states being added to previously existing states.

The inventive compounds can be used to treat a large number of signs, symptoms and/or dysfunctions associated with the disorders of the central nervous system and in particular the aforementioned states. These include for example a distorted relation to reality, lack of insight and the ability to comply with the usual social norms and demands of life, changes in behavior, changes in individual urges such as hunger, sleep, thirst etc. and in mood, disorders of memory and association, personality changes, especially emotional lability, hallucinations, ego disturbances, incoherence of thought, ambivalence, autism, depersonalization or hallucinations, delusional ideas, staccato speech, absence of associated movement, small-step gait, bent posture of trunk and limbs, tremor, mask-like face, monotonous speech, depression, apathy, deficient spontaneity and irresolution, reduced association-ability, anxiety, nervous agitation, stammering, social phobia, panic disorders, withdrawal syndromes associated with dependence, expansive syndromes, states of agitation and confusion, dysphoria, dyskinetic syndromes and tic disorders, e.g. Huntington's chorea, Gilles de la Tourette syndrome, vertigo syndromes, e.g. peripheral postural, rotational and vestibular vertigo, melancholia, hysteria, hypochondria and the like.

A treatment in the sense according to the invention includes not only the treatment of acute or chronic signs, symptoms and/or dysfunctions but also a preventive treatment (prophylaxis), in particular as recurrence or episode prophylaxis. The treatment may be symptomatic, for example directed at suppression of symptom. It may take place short-term, be directed at the medium term or may also be a long-term treatment, for example as part of maintenance therapy.

The inventive compounds are preferably suitable for the treatment of disorders of the central nervous system, especially for the treatment of affective disorders; neurotic disorders, stress disorders and somatoform disorders and psychoses and specifically for the treatment of schizophrenia and depression. Owing to their high selectivity in relation to the $D_3$ receptor, the inventive triazole compounds are also for the treatment of renal function disorders, especially of renal function disorders caused by diabetes mellitus (WO 00/67847).

The inventive use of the described compounds comprises a method within the scope of the treatment. This entails the individual to be treated, preferably a mammal, in particular a human or agricultural or domestic animal, being given an effective amount of one or more compounds, usually formulated in accordance with pharmaceutical and veterinary practice. Whether such a treatment is indicated, and the form it is to take, depends on the individual case and is subject to a medical assessment (diagnosis) which takes account of the signs, symptoms and/or dysfunctions present, the risks of developing certain signs, symptoms and/or dysfunctions, and other factors.

The treatment usually takes place by administration once or more than once a day, where appropriate together or alternately with other active ingredients or active ingredient-containing products, so that an individual to be treated is given a daily dose preferably of about 1 to 1000 mg/kg of body weight on oral administration or of about 0.1 to 100 mg/kg of body weight on parenteral administration.

The invention also relates to the production of pharmaceutical compositions for the treatment of an individual, preferably a mammal, in particular a human or agricultural or domestic animal. Thus, the ligands are usually administered in the form of pharmaceutical compositions which comprise a pharmaceutically acceptable excipient with at least one ligand of the invention and, where appropriate, further active ingredients. These compositions can be administered for example by the oral, rectal, transdermal, subcutaneous, intravenous, intramuscular or intranasal route.

Examples of suitable pharmaceutical formulations are solid pharmaceutical forms such as oral powders, dusting powders, granules, tablets, especially film-coated tablets, pastilles, sachets, cachets, sugar-coated tablets, capsules such as hard and soft gelatin capsules, suppositories or vaginal pharmaceutical forms, semisolid pharmaceutical forms such as ointments, creams, hydrogels, pastes or patches, and liquid pharmaceutical forms such as solutions, emulsions, especially oil-in-water emulsions, suspensions, for example lotions, preparations for injection and infusion, eye drops and ear drops. Implanted delivery devices can also be used to administer inhibitors of the invention. A further possibility is also to use liposomes or microspheres.

The compositions are produced by mixing or diluting inhibitors of the invention usually with an excipient. Excipients may be solid, semisolid or liquid materials which serve as vehicle, carrier or medium for the active ingredient.

Suitable excipients are listed in the relevant pharmaceutical monographs. The formulations may additionally comprise pharmaceutically acceptable carriers or conventional excipients such as lubricants; wetting agents; emulsifying and suspending agents; preservatives; antioxidants; antiirritants; chelating agents; tablet-coating aids; emulsion stabilizers; film formers; gel formers; odor-masking agents; masking flavors; resins; hydrocolloids; solvents; solubilizers; neutralizers; permeation promoters; pigments; quaternary ammonium compounds; refatting and super-fatting agents; ointment, cream or oil bases; silicone derivatives; spreading aids; stabilizers; sterilants; suppository bases; tablet excipients, such as binders, fillers, lubricants, disintegrants or coatings; propellants; desiccants; opacifiers; thickeners; waxes; plasticizers; white oils. An arrangement concerning this is based on expert knowledge as set forth for example in Fiedler, H. P., Lexikon der Hilfsstoffe für Pharmazie, Kosmetik und angrenzende Gebiete, 4th edition, Aulendorf: ECV-Editio-Kantor-Verlag, 1996.

The following examples serve to illustrate the invention without limiting it.

PREPARATION EXAMPLES

Example I

2-{3-[(4-methyl-5-phenyl-4H-1,2,4-triazol-3-yl)thio] propyl}-7-propionyl-1,2,3,4-tetrahydroisoquinoline (hydrochloride)—compound Ia'-25 as hydrochloride 1.1 2-(Trifluoroacetyl)-1,2,3,4-tetrahydroisoquinoline Trifluoroacetic anhydride (2.13 mol, 452.0 g) was introduced into dichloromethane (452 ml) at 10-15° C. At this temperature, a solution of tetrahydroisoquinoline (1.94 mol, 268.3 g) in dichloromethane (90 ml) was added thereto. The reaction mixture was stirred at room temperature overnight and then hydrolyzed with ice water (813 g). After stirring for 1 h, the phases were separated. The organic phase was washed successively with water (813 ml), with half-concentrated $NaHCO_3$ solution (550 ml) and again with water (500 ml). It was then concentrated under reduced pressure, resulting in 446 g of crude product which was employed in the following reaction.

1.2 1-[2-(Trifluoroacetyl)-1,2,3,4-tetrahydroisoquinolin-7-yl]propan-1-one

Aluminum trichloride (0.78 mol, 103.7 g) was suspended in dichloromethane (93 ml) at 10-15° C., then while cooling at this temperature, the tri-fluoroacetyltetrahydrosoquinoline from step 1.1 (2.13 mol, 452.0 g) and propionyl chloride (0.47 mol, 43.2 g) were successively added. The mixture was then heated to reflux and maintained at the temperature for 5 h. It was then cooled to 5-10° C. and diluted with 70 ml of dichloromethane. Prepared in a 2 flask. The reaction solution was then rapidly introduced into a mixture of 1000 g of ice and 500 ml of methyl tert-butyl ether while cooling in an ice bath. After 30 min, the phases were separated and the organic phase was washed successively with 500 ml of water, with 500 ml of half-concentrated $NaHCO_3$ solution and again with 300 ml of water. The organic phase was then concentrated under reduced pressure, resulting in 89.9 g of a mixture of the title compound with its 6 isomer (isomer ratio 7 isomer:6 isomer: about 75:25 (by means of $^{13}C$-NMR)) which was employed in the following stage.

1.3 7-Propionyl-1,2,3,4-tetrahydroisoquinoline (hydrochloride)

The product from step 1.2 (0.39 mol, 111.0 g) was dissolved in n-propanol (744 ml), and hydrochloric acid (32% strength, 3.5 mol, 400 g) was added thereto. The mixture was then heated to reflux for 5 h. A further 300 ml of n-propanol were then added, and water was removed by azeotropic distillation using n-propanol. In total, 890 ml of distillate were distilled out. During this, the hydrochloride of the propionyl-isoquinoline out; a further 1500 ml of n-propanol were added and again distilled out. Then 1200 ml of methyl tert-butyl ether were added, and the mixture was cooled to 5° C. and stirred for 30 min. The resulting solid was filtered off and dried in vacuo at 40-50° C. 82.9 g of a mixture of 6- and 7-propionyl-1,2,3,4-tetrahydroisoquinoline was obtained in this way as hydrochloride with a 7 isomer:6 isomer ratio of isomers of about 80:20 (determined by means of $^{13}C$-NMR)).

1.4 1-[2-(3-Chloropropyl)-1,2,3,4-tetrahydroisoquinolin-7-yl]propan-1-one

The isomer mixture from step 1.3 (0.27 mol, 63.4 g) was suspended in 634 ml of dichloromethane. The base was liberated from the hydrochloride by adding 1.05 eq of sodium hydroxide solution and 317 ml of water and separating the phases. After phase separation and extraction of the aqueous phase with a little dichloromethane, the combined organic phases were washed once with 50 ml of water, filtered and concentrated several times in a rotary evaporator. The residue was dissolved in dimethylformamide, and 1-bromo-3-chlorpropane (0.68 mol, 107.4 g) and triethylamine (0.55 mol, 55.3 g) were added successively to the solution. It was then stirred at room temperature for 16 h, 760 ml of water were added to the resulting suspension, and it was extracted twice with about 300 ml of dichloromethane. The combined organic phases were washed once with 100 ml of water, filtered and concentrated under reduced pressure. The residue was dissolved in 61 ml of methanol and 410 ml of methyl tert-butyl ether. 1.2 equivalents of hydrogen chloride in isopropanol are added drop-wise thereto. The mixture was briefly boiled and then slowly cooled to room temperature. The precipitate was filtered filtered off sucked air through until it was good. This resulted in 87 g of crude product which was recrystallized twice from methanol. This resulted in 26.7 g of the title compound (7 isomer:6 isomer: 97:3 (via $^{13}$C-NMR)).

1.5 Potassium 4-methyl-5-phenyl-4H-1,2,4-triazole-3-thiolate

Methyl isothiocyanate (0.75 mol, 54.5 g) and potassium carbonate (0.73 mol, 101.5 g) were introduced into ethanol (1.8 ). Benzoyl hydrazide (0.73 mol, 100.0 g) was added thereto at room temperature. The yellowish suspension was heated to reflux for 3 h and filtered with suction, and the filter was washed with methanol. The filtrate was concentrated and stirred with dichloromethane/methanol (1% by volume). This resulted in 89.4 g of the title compound as pale solid. The filter cake was dissolved in water (400 ml) and extracted with ethyl acetate and dichloromethane. The organic phase was dried, filtered and concentrated. This resulted in a further 44.4 g of the title compound as pale solid. Yield: 133.8 g.

1.5 2-{3-[(4-Methyl-5-phenyl-4H-1,2,4-triazol-3-yl)-thio]propyl}-7-propionyl-1,2,3,4-tetrahydroisoquinoline (hydrochloride)

1.00 g (3.76 mmol) of potassium 4-methyl-5-phenyl-4H-1,2,4-triazole-3-thiolate from step 1.4 and 0.90 g of 1-[2-(3-chloropropyl)-1,2,3,4-tetrahydroisoquinolin-7-yl]propan-1-one (3.92 mmol) from step 1.4 were stirred with triethylamine (5.77 mmol, 0.58 g) in dimethylformamide (30 ml) at room temperature overnight. For workup, a brine was added, the mixture was extracted with ethyl acetate, the combined organic phases were dried, and the solvent was removed. This resulted in 1.5 g of a dark brown oil which contains the title compound as free base. The hydrochloride was obtained therefrom by precipitation from isopropanol HCl. This resulted in 0.7 g of the title compound as beige-colored solid with a melting point of 181-184° C.

EI-MS [M$^+$]=420;

$^1$H-NMR (270 MHz, DMSO) δ ppm: 7.94-7.52 (m, 7H), 7.41 (d, 1H), 4.79-4.52 (m, br., 1H), 4.47-4.25 (m br., 1H), 3.71 (m, br., 1H), 3.63 (s, 3H), 3.49-3.21 (m, 6H), 3.12 (m, br., 1H), 3.01 (m sym., 2H), 2.27 (quint., 2H), 1.07 (t, 3H).

Example 2

2-(3-{[4-Methyl-5-(1-methyl-1H-pyrrol-2-yl)-4H-1,2,4-triazol-3-yl]thio}propyl)-7-propionyl-1,2,3,4-tetrahydroisoquinoline (hydrochloride)—compound Ia'-15 as hydrochloride 20.38 g (0.1 mol) of methyl-5-(1-methyl-1H-pyrrol-2-yl)-4H-1,2,4-triazole-3-thiol (Rappoport et al. J. Org. Chem 37 (1972) 3618) was introduced together with lithium hydroxide (0.36 mol, 8.65 g) into dimethylformamide (130 ml). 26.00 g (86 mmol) of the compound from example 1.4 were added as solid thereto. The reaction mixture was stirred at room temperature for about 2.5-3 days to achieve maximal conversion. For workup, the reaction mixture was mixed with 390 ml of water and extracted twice with 130 ml of methyl tert-butyl ether/ethyl acetate (1:1 vol/vol). The combined organic phases were washed with 100 ml of dilute brine. The organic phase was stirred with activated carbon and then filtered. 39.8 g of crude product by concentration of the filtrate. The crude product was dissolved in 138 ml of methanol and, at room temperature, 3 equivalents of hydrogen chloride, based on the compound from example 1.4 employed, were added thereto as solution in isopropanol, and the resulting suspension was stirred overnight and then cooled to 5° C. cooled and the solid is filtered off. The solid was dried in vacuo at 40-50° C., resulting in 24.7 g of the title compound as hydrochloride which was recrystallized from methanol (59 ml). The product was again dried in vacuo at 40-50° C., resulting in 16.4 g of the title compound as hydrochloride with a melting point of 181-184° C.

EI-MS [M$^+$]=423; $^1$H-NMR (270 MHz, DMSO) δ ppm: 7.91-7.78 (m, 2H), 7.39 (d, 1H), 7.08 (s, 1H), 6.62 (m, 1H), 6.22 (m, 1H), 4.77-4.50 (m, br., 1H), 3.78 (s, 3H), 3.71 (m, br., 1H), 3.62 (s, 3H), 3.32 (m, 6H), 3.11 (m, br., 1H), 3.01 (m sym., 2H), 2.27 (quint., 2H), 1.07 (t, 3H).

Example 3

7-Benzoyl-2-{3-[(4-methyl-5-phenyl-4H-1,2,4-triazol-3-yl)thio]propyl}-1,2,3,4-tetrahydroisoquinolines (hydrochloride)—compound Ia'-19 as hydrochloride 3.1 N-(2-Phenylethyl)acetamide Phenethylamine (206.30 mmol, 25.00 g) was introduced into toluene (300 ml). Acetyl chloride (252.23 mmol, 19.80 g) was added dropwise, and the mixture was stirred at room temperature overnight.

The reaction mixture was poured into water, and the aqueous mixture was extracted with ethyl acetate. The organic phase was washed with saturated aqueous brine, dried and concentrated. 32.7 g of the title compound were obtained as a brown oil which was chromatographed on silica gel (mobile phase dichloromethane with 1% methanol) and stirred in hexane. This resulted in 27.6 g of the title compound with a melting point of 50-53° C.

3.2 N-[2-(4-Benzoylphenyl)ethyl]acetamide

N-(2-Phenylethyl)acetamide (49.01 mmol, 8.00 g) was introduced into nitrobenzene (40 ml). Benzoyl chloride (54.07 mmol, 7.60 g) was added thereto and then, at room temperature, aluminum tri-chloride (73.52 mmol, 9.80 g) was introduced in portions. The mixture was then heated at 50° C. for 8 h. The reaction mixture was poured into a mixture of ice and concentrated hydrochloric acid, and nitrobenzene was removed by steam distillation. The aqueous residue was extracted with ethyl acetate. The residue after concentration of the organic phase was chromatographed on silica gel (mobile phase dichloromethane/methanol (3% by volume)), resulting in 4.5 g of the title compound as orange oil.

3.3 (2-Acetyl-1,2,3,4-tetrahydroisoquinolin-7-yl)-(phenyl)methanone

N-[2-(4-Benzoylphenyl)ethyl]acetamide (16.46 mmol, 4.40 g) was introduced into glacial acetic acid (20 ml). Concentrated sulfuric acid (25 ml) and then formalin (49.29 mmol, 4.00 g) were slowly added thereto at 30° C. The mixture was stirred for 2 days and poured into ice-water, and the aqueous phase was extracted with ethyl acetate. The organic phase was washed with aqueous sodium carbonate solution, dried and concentrated. The residue was stirred with diethyl ether and the solid resulting therefrom was filtered off with suction. 1.6 g of the title compound were obtained as a beige-colored solid with a melting point of 110-113° C.

3.4 Phenyl(1,2,3,4-tetrahydroisoquinolin-7-yl)-methanone (2-Acetyl-1,2,3,4-tetrahydroisoquinolin-7-yl)-(phenyl)methanone (11.10 mmol, 3.10 g) was heated in hydrochloric acid (7 M, 250 ml) to reflux for 6 h. The resulting mixture was concentrated, made alkaline with sodium hydroxide solution and extracted with ethyl acetate. Drying of the organic phase and concentration resulted in 1.7 g of the title compound as a brown oil.

3.5 [2-(3-Chloropropyl)-1,2,3,4-tetrahydroisoquinolin-7-yl](phenyl)methanone

In analogy to the method for step 1.4 from example 1, 1.3 g of the title compound were obtained as an orange oil starting from phenyl(1,2,3,4-tetrahydroisoquinolin-7-yl)methanone (7.16 mmol, 1.70 g).

3.6 7-Benzoyl-2-{3-[(4-methyl-5-phenyl-4H-1,2,4-triazol-3-yl)thio]propyl}-1,2,3,4-tetrahydroisoquinoline (hydrochloride)

In analogy to the method for example 2, 0.50 g of the title compound was obtained as a beige-colored solid with a melting point of 146-152° C. by reacting the compound obtained in stage 3.5 (2.23 mmol, 0.70 g) with the triazole from step 1.5 (2.35 mmol, 0.45 g).

$^1$H-NMR (270 MHz, DMSO) δ ppm: 7.81-7.50 (m, 12H), 7.44 (d, 1H), 4.79-4.53 (m, br., 1H), 4.48-4.26 (m br., 1H), 3.66 (s, 3H), 3.37 (m, 6H), 3.16 (m, br., 1H), 2.28 (quint., 2H).

Example 4

7-Benzoyl-2-{4-[(4-methyl-5-phenyl-4H-1,2,4-triazol-3-yl)thio]butyl}-1,2,3,4-tetrahydroisoquinolines (hydrochloride)—compound Ia'-77 as hydrochloride 4.1 3-[(4,4-Dimethoxybutyl)thio]-4-methyl-5-phenyl-4H-1,2,4-triazole The triazole from step 1.5 (43.60 mmol, 10.00 g) and 4-chloro-1,1-dimethoxybutane (44.55 mmol, 6.80 g) were stirred at 80° C. for 10 h. The reaction mixture was poured into water and extracted with ethyl acetate. The organic phase was washed with aqueous brine, dried and concentrated. The residue was purified by chromatography (mobile phase: ethyl acetate). 6.3 g of the title compound were obtained as a colorless oil.

4.2 4-[(4-Methyl-5-phenyl-4H-1,2,4-triazol-3-yl)thio]butanal

Concentrated sulfuric acid was added to a solution of 3-[(4,4-dimethoxybutyl)thio]-4-methyl-5-phenyl-4H-1,2,4-triazole (20.49 mmol, 6.30 g) in ethanol (50 ml) until cloudy. The mixture was stirred at 40° C. for 2 h and then made alkaline with sodium carbonate and subsequently extracted with ethyl acetate. The organic phase was dried and concentrated, resulting in 4.8 g of the title compound colorless oil.

4.3 7-Benzoyl-2-{4-[(4-methyl-5-phenyl-4H-1,2,4-triazol-3-yl)thio]butyl}-1,2,3,4-tetrahydroisoquinolines (hydrochloride)

4-[(4-Methyl-5-phenyl-4H-1,2,4-triazol-3-yl)thio]butanal (3.83 mmol, 1.00 g), the hydrochloride from step 3.3 (3.65 mmol, 1.00 g) and glacial acetic acid (14.99 mmol, 0.90 g) were introduced into methanol. NaCNBH$_3$ (4.77 mmol, 0.30 g) was added thereto in portions at room temperature. The mixture was stirred at room temperature overnight and then poured into water. The mixture was made alkaline with Na$_2$CO$_3$ and extracted with ethyl acetate. The organic phase was washed with an aqueous brine, dried and concentrated, resulting in 1.7 g of an orange-colored oil which was purified by chromatography on silica gel (mobile phase: dichloromethane/methanol (1.5-3.5% by volume)). 1.1 g of the free base of the title compound were obtained as a yellow oil which was converted with hydrogen chloride in isopropanol into the hydrochloride. 0.9 g of hydrochloride was obtained as a white solid with a melting point of 171° C.

$^1$H-NMR (360 MHz, DMSO) δ ppm: 7.77-7.52 (m, 12H), 7.42 (d, 1H), 4.63 (d br., 1H), 4.41-4.23 (m, br., 1H), 3.69 (s, br., 1H), 3.61 (s, 3H), 3.42-3.04 (m, 7H), 1.94 (quint., 2H), 1.80 (quint., 2H).

Example 5

7-Benzoyl-2-(3-{[4-methyl-5-(1-methyl-1H-pyrrol-2-yl)-4H-1,2,4-triazol-3-yl]thio}propyl)-1,2,3,4-tetrahydroisoquinoline (hydrochloride)—compound Ia'-12 as hydrochloride In analogy to the method for example 2, 0.18 g of the title compound was obtained as a white solid with a melting point of 138° C. by reacting the compound prepared in step 3.5 (1.59 mmol, 0.50 g) with methyl-5-(1-methyl-1H-pyrrol-2-yl)-4H-1,2,4-triazole-3-thiol (1.54 mmol, 0.30 g).

$^1$H-NMR (360 MHz, DMSO) δ ppm: 7.75-7.50 (m, 7H), 7.42 (d, 1H), 7.03 (s, 1H), 6.55 (m, 1H), 6.17 (m, 1H), 4.67 (s, br., 1H), 4.37 (s, br., 1H), 3.76 (s br., 3+1H), 3.60 (s, 3H), 3.30 (m, 6H), 3.15 (s br., 1H), 2.27 (quint., 2H).

Example 6

7-Benzoyl-2-(3-{[4-methyl-5-(1H-pyrrol-2-yl)-4H-1,2,4-triazol-3-yl]thio}propyl)-1,2,3,4-tetrahydroisoquinoline (hydrochloride)—compound Ia'-64 as hydrochloride In analogy to the method indicated for example 2, 0.20 g of the title compound was obtained as a white solid with a melting point of 163° C. by reacting 4-methyl-5-(1H-pyrrol-2-yl)-4H-1,2,4-triazole-3-thiol (1.59 mmol, 0.50 g) with the tetrahydroisoquinoline compound prepared in step 3.5 (1.66 mmol, 0.30 g);

$^1$H-NMR (360 MHz, DMSO) δ ppm: 7.73-7.52 (m, 7H), 7.41 (d, 1H), 7.05 (s, 1H), 6.74 (m, 1H), 6.27 (m, 1H), 4.64 (s, br., 1H), 4.36 (s, br., 1H), 3.71 (s, 3H), 3.41-3.21 (m, 5H), 3.15 (m, br., 1H), 2.19 (quint., 2H).

Example 7

7-Benzoyl-2-(3-{[5-(2-furyl)-4-methyl-4H-1,2,4-triazol-3-yl]thio}propyl)-1,2,3,4-tetrahydroisoquinoline (hydrochloride)—compound Ia'.3 as hydrochloride In analogy to the method indicated for example 2, 0.10 g of the title compound was obtained as a yellowish solid with a melting point of 180-185° C. by reacting the tetrahydroisoquinoline compound prepared in step 3.5 (1.27 mmol, 0.40 g) and 5-(2-furyl)-4-methyl-4H-1,2,4-triazole-3-thiol (1.38 mmol, 0.25 g; preparation in analogy to step 2.3);

$^1$H-NMR (360 MHz, DMSO) δ ppm: 7.96 (s, 1H), 7.76-7.54 (m, 7H), 7.43 (m, 1H), 7.09 (m, 1H), 6.73 (m, 1H), 4.69 (d br., 1H), 4.44-4.27 (m, br., 1H), 3.72 (s, 3H), 3.35 (m, br., 2H), 3.28 (m, 6H), 3.16 (m br., 1H), 2.20 (quint., 2H).

Example 8

7-Benzoyl-2-{3-[(4-methyl-5-thien-3-yl-4H-1,2,4-triazol-3-yl)thio]propyl}-1,2,3,4-tetrahydroisoquinoline (hydrochloride)—compound Ia'-18 as hydrochloride In analogy to the method indicated for example 2, 0.10 g of the title compound was obtained as a yellowish solid with a melting point of 140° C. by reacting the tetrahydroisoquinoline compound prepared in step 3.5 (1.27 mmol, 0.40 g) and sodium 4-methyl-5-thien-2-yl-4H-1,2,4-triazole-3-thiolate (1.37 mmol, 0.30 g; preparation in analogy to step 1.5);
EI-MS [M$^+$]=474; $^1$H-NMR (360 MHz, DMSO) δ ppm: 11.10 (s, br., 1H), 8.15 (s, 1H), 7.84-7.55 (m, 9H), 7.45 (d, 1H), 4.68 (s, br., 1H), 4.39 (s, br., 1H), 3.71 (s, 3H), 3.50-3.24 (m, 6H), 3.19 (m, br., 1H), 2.25 (quint., 2H).

Example 9

7-Benzoyl-2-{3-[(4-methyl-5-pyridin-3-yl-4H-1,2,4-triazol-3-yl)thio]propyl}-1,2,3,4-tetrahydroisoquinoline (hydrochloride)—compound Ia'-64 as hydrochloride In analogy to the method indicated for example 2, 0.17 g of the title compound was obtained as a white solid with a melting point of 148° C. by reacting the tetrahydroisoquinoline compound prepared in step 3.5 (1.27 mmol, 0.40 g) and 3-(5-mercapto-4-methyl-4H-1,2,4-triazol-3-yl)pyridinium chloride (1.31 mmol, 0.30 g; preparation in analogy to step 2.3); $^1$H-NMR (360 MHz, DMSO) δ ppm: 9.00 (s, 1H), 8.83 (m, 1H), 8.33 (m, 1H), 7.78-7.53 (m, 8H), 7.44 (d, 1H), 4.75-4.62 (m, br., 1H), 4.43-4.29 (m, br., 1H), 3.73 (m, br., 1H), 3.68 (s, 3H), 3.43 (m, 6H), 3.19-3.08 (m, 1H), 2.25 (quint., 2H).

Example 10

7-Benzoyl-2-{3-[(4-methyl-5-pyridin-4-yl-4H-1,2,4-triazol-3-yl)thio]propyl}-1,2,3,4-tetrahydroisoquinoline (hydrochloride)—compound Ia'-1 as hydrochloride In analogy to the method indicated for example 2, 0.30 g of the title compound was obtained as a yellowish solid with a melting point of 140-146° C. by reacting the tetrahydroisoquinoline compound prepared in step 3.5 (1.27 mmol, 0.40 g) and 4-(5-mercapto-4-methyl-4H-1,2,4-triazol-3-yl)pyridinium chloride (1.31 mmol, 0.30 g; preparation in analogy to step 2.3);
$^1$H-NMR (360 MHz, DMSO) δ ppm: 11.40 (s, br., 1H), 8.95 (m, 2H), 8.10 (m, 2H), 7.79-7.56 (m, 7H), 7.45 (d, 1H), 4.81-4.13 (m, 2H), 3.79 (s, 3H), 3.79-3.69 (m, 1H), 3.48-3.29 (m, 6H), 3.22-3.10 (m, 1H), 2.35 (quint., 2H).

Example 11

7-(3-Fluorobenzoyl)-2-{3-[(4-methyl-5-pyrazin-2-yl-4H-1,2,4-triazol-3-yl)thio]propyl}-1,2,3,4-tetrahydroisoquinoline (hydrochloride)—compound Ia'-58 as hydrochloride 11.1 N-{2-[4-(3-Fluorobenzoyl)phenyl]ethyl}acetamide
In analogy to the method indicated for step 3.2, 8.60 g of N-{2-[4-(3-fluorobenzoyl)phenyl]ethyl}acetamide were obtained as a beige-colored solid with a melting point of 78° C. by reacting the compound prepared in step 3.1 (61.27 mmol, 10.00 g) with 3-fluorobenzoyl chloride (67.48 mmol, 10.70 g).

11.2 (2-Acetyl-1,2,3,4-tetrahydroisoquinolin-7-yl)(3-fluorophenyl)methanone
In analogy to the method indicated for step 3.3, 2.60 g of the title compound were prepared from N-{2-[4-(3-fluorobenzoyl)phenyl]ethyl}acetamide (5.60 g, 19.63 mmol); beige solid, melting point 136-139° C.

11.3 7-(3-Fluorobenzoyl)-1,2,3,4-tetrahydroisoquinoline (hydrochloride)
In analogy to the method indicated for step 3.3, 2.20 g of the title compound were prepared from the compound obtained in step 11.2 (8.74 mmol, 2.60 g); beige solid, melting point 219-223° C.

11.4 [2-(3-Chloropropyl)-1,2,3,4-tetrahydroisoquinoline-7-yl](3-fluorophenyl)methanone
In analogy to the method indicated for step 3.4, 2.20 g of the title compound were prepared from the compound obtained in step 11.3 (7.54 mmol, 2.20 g); orange oil.

11.5 7-(3-Fluorobenzoyl)-2-{3-[(4-methyl-5-pyrazin-2-yl-4H-1,2,4-triazol-3-yl)thio]propyl}-1,2,3,4-tetrahydroisoquinolines (hydrochloride)
In analogy to the method indicated for example 2, 0.20 g of the title compound was obtained as a white solid, which was recrystallized from isopropanol/water 98:2, by reacting the tetrahydroisoquinoline compound prepared in step 11.4 (1.27 mmol, 0.40 g) and (1.51 mmol, 0.50 g) and 4-methyl-5-pyrazin-2-yl-4H-1,2,4-triazole-3-thiol (1.55 mmol, 0.30 g); EI-MS [M$^+$]=488.

Example 12

7-(3-Fluorobenzoyl)-2-{3-[(4-methyl-5-pyridin-3-yl-4H-1,2,4-triazol-3-yl)thio]propyl}-1,2,3,4-tetrahydroisoquinolines (hydrochloride)—compound Ia'-63 as hydrochloride In analogy to the method indicated for example 2, 0.45 g of the title compound was obtained as a beige-colored solid with a melting point of 133° C. by reacting the tetrahydroisoquinoline compound prepared in step 11.4 (1.81 mmol, 0.60 g) and 3-(5-mercapto-4-methyl-4H-1,2,4-triazol-3-yl)pyridinium chloride (1.75 mmol, 0.40 g; preparation in analogy to step 2.3);
$^1$H-NMR (360 MHz, DMSO) δ ppm: 11.54 (s, br., 1H), 9.10 (s, 1H), 8.89 (m sym., 1H), 8.49 (m, 1H), 7.88 (m, 1H), 7.67-7.39 (m, 7H), 4.66 (m, br., 1H), 4.41-4.31 (m, 1H), 3.70 (s, 3H), 3.46-3.27 (m, 6H), 3.12 (d br., 1H), 2.28 (quint., 2H).

Example 13

7-Acetyl-2-{3-[(4-methyl-5-thien-3-yl-4H-1,2,4-triazol-3-yl)thio]propyl}-1,2,3,4-tetrahydroisoquinoline (hydrochloride)—compound Ia'-13 as hydrochloride 13.1 1-[2-(Trifluoroacetyl)-1,2,3,4-tetrahydroisoquinoline-7-yl]ethanone
2-(Trifluoroacetyl)-1,2,3,4-tetrahydroisoquinoline (140 mmol, 32.00 g) was introduced into $CS_2$ (190 ml). Aluminum trichloride (837 mmol, 111.60 g) was added thereto in portions at room temperature. Acetyl chloride (419.12 mmol, 32.90 g) was then added dropwise in such a way that gentle refluxing took place, and the mixture was heated to reflux for a further hour. The reaction mixture was poured into ice-water and extracted with dichloromethane. The organic phase was dried, filtered with suction and concentrated and then stirred with isopropanol. 22 g of the title compound were obtained with a melting point of 80° C.

13.2 7-Acetyl-1,2,3,4-tetrahydroisoquinoline (hydrochloride)

In analogy to the method indicated for step 1.3, 3.80 g of the title compound (yellow solid) were prepared from the compound obtained in step 13.1 (22.12 mmol, 6.00 g).

13.3 1-[2-(3-Chloropropyl)-1,2,3,4-tetrahydroisoquinoline-7-yl]ethanone

In analogy to the method indicated for step 1.4, 3.00 g of the title compound (yellow oil) were prepared from the compound obtained in step 13.2 (17 mmol, 3.60 g).

13.4 7-Acetyl-2-{3-[(4-methyl-5-thien-3-yl-4H-1,2,4-triazol-3-yl)thio]propyl}-1,2,3,4-tetrahydroisoquinoline (hydrochloride)

In analogy to the method indicated for step 1.6, 0.20 g of the title compound was obtained by reacting the tetrahydroisoquinoline compound prepared in step 13.3 (1.99 mmol, 0.50 g) with sodium 4-methyl-5-thien-2-yl-4H-1,2,4-triazol-3-thiolate (2.28 mmol, 0.50 g; preparation in analogy to step 1.5); EI-MS [M$^+$]=412.

Example 14

7-(3-Fluorobenzoyl)-2-{3-[(4-methyl-5-phenyl-4H-1,2,4-triazol-3-yl)thio]propyl}-1,2,3,4-tetrahydroisoquinolines (hydrochloride)—compound Ia'-39 as hydrochloride In analogy to the method indicated for example 2, 0.45 g of the title compound was obtained as a beige-colored solid with a melting point of 147° C. by reacting the tetrahydroisoquinoline compound prepared in step 11.4 (1.51 mmol, 0.50 g) with the triazole compound from step 1.5 (1.51 mmol, 0.35 g);

EI-MS [M$^+$]=486; $^1$H-NMR (360 MHz, DMSO) δ ppm: 7.80-7.43 (m, 12H), 4.77-4.58 (m, br., 1H), 4.45-4.27 (m, br., 1H), 3.64 (s, 1H), 3.46-3.22 (m, 6H), 3.15 (m, br., 1H), 2.24 (quint., 2H).

Example 15

7-(3-Fluorobenzoyl)-2-(3-{[4-methyl-5-(1-methyl-1H-pyrrol-2-yl)-4H-1,2,4-triazol-3-yl]thio}-propyl)-1,2,3,4-tetrahydroisoquinoline (hydrochloride) compound Ia'-60 as hydrochloride In analogy to the method indicated for example 2, 0.15 g of the title compound was obtained as a beige-colored solid with a melting point of 139° C. by reacting the tetrahydroisoquinoline compound prepared in step 11.4 (1.81 mmol, 0.60 g) with the triazole compound from step 2.4 (1.81 mmol, 0.35 g);

$^1$H-NMR (400 MHz, DMSO) δ ppm: 11.78 (s, br., 1H), 7.70-7.41 (m, 7H), 7.12 (s, 1H), 6.67 (s, 1H), 6.23 (m, 1H), 4.75-4.60 (m, 1H), 4.47-4.31 (m, 1H), 3.81 (s, 3H), 3.64 (s, 3H), 3.52-3.30 (m, 6H), 3.19-3.06 (m, br., 1H), 2.31 (quint., 2H).

Example 16

1-[2-(3-{[5-(1-Benzothien-2-yl)-4-methyl-4H-1,2,4-triazol-3-yl]thio}propyl)-1,2,3,4-tetrahydroisoquinolin-7-yl]propan-1-one (compound Ia'-57)

16.1 5-(1-Benzothien-2-yl)-4-methyl-4H-1,2,4-triazole-3-thiol 2-(1-Benzothien-2-ylcarbonyl)-N-methylhydrazine-carbothioamide (15.30 mmol, 4.06 g) and 50 ml of 2N sodium hydroxide solution were heated to reflux for 8 h. The reaction mixture was diluted with water and extracted three times with ethyl acetate. The aqueous phase was acidified with 2N hydrochloric acid and extracted with dichloromethane. The crude product obtained after drying and concentration of the organic phase was purified by chromatography on silica gel (mobile phase: cyclohexane/ethyl acetate 6:4), resulting in 2.2 g of the title compound.

16.2 1-[2-(3-{[5-(1-Benzothien-2-yl)-4-methyl-4H-1,2,4-triazol-3-yl]thio}propyl)-1,2,3,4-tetrahydroisoquinoline-7-yl]propan-1-one In analogy to the method indicated for example 2, 0.37 g of the title compound was obtained by reacting the triazole compound prepared in step 16.1 (2.02 mmol, 0.50 g) and the isoquinoline compound from step 1.4 (2.02 mmol, 0.54 g); EI-MS [M$^+$]=476.

Example 17

2-(3-{[5-(1,3-Benzothiazol-2-yl)-4-methyl-4H-1,2,4-triazol-3-yl]thio}propyl)-7-propionyl-1,2,3,4-tetrahydroisoquinolines (hydrochloride)—compound Ia'-70 as hydrochloride In analogy to the method indicated for example 2, 0.47 g of the title compound was obtained by reacting 5-(1,3-benzothiazol-2-yl)-4-methyl-4H-1,2,4-triazole-3-thiol (4.87 mmol, 1.21 g; preparation in analogy to step 16.1) and the isoquinoline compound from step 1.4 (4.87 mmol, 1.30 g); EI-MS [M$^+$]=477.

Example 18

7-Acetyl-2-(3-{[4-methyl-5-(1-methyl-1H-pyrrol-2-yl)-4H-1,2,4-triazol-3-yl]thio}propyl)-1,2,3,4-tetrahydroisoquinoline (hydrochloride)—compound Ia'-4 as hydrochloride In analogy to the method indicated for example 2, 0.7 g of the title compound was obtained as a beige-colored solid with a melting point of 152-158° C. by reacting the tetrahydroisoquinoline compound prepared in step 13.3 (2.78 mmol, 0.70 g) with methyl-5-(1-methyl-1H-pyrrol-2-yl)-4H-1,2,4-triazole-3-thiol (2.83 mmol, 0.55 g);

$^1$H-NMR (270 MHz, DMSO) δ ppm: 11.20 (s, br., 1H), 7.91-7.78 (m, 2H), 7.40 (d, 1H), 7.07 (s, 1H), 6.60 (m, 1H), 6.22 (t, 1H), 4.76-4.54 (m, br., 1H), 4.45-4.23 (m, br., 1H), 3.60 (s, 3H), 3.45-3.19 (m, 6H), 3.12 (m, br., 1H), 2.55 (s, 3H), 2.26 (quint., 2H).

Example 19

7-Acetyl-2-{3-[(4-methyl-5-pyridin-3-yl-4H-1,2,4-triazol-3-yl)thio]propyl}-1,2,3,4-tetrahydroisoquinolines (hydrochloride)—compound Ia'-39 as hydrochloride In analogy to the method indicated for example 2, 0.8 g of the title compound was obtained as a pale solid by reacting the tetrahydroisoquinoline compound prepared in step 13.3 (5.16 mmol, 1.30 g) with 4-methyl-5-pyridin-3-yl-4H-1,2,4-triazole-3-thiol hydrochloride (5.47 mmol, 1.25 g; preparation in analogy to step 2.3); EI-MS [M$^+$]=407.

Example 20

1-{2-[3-(4-Methyl-5-pyridin-2-yl-4H-[1,2,4]triazol-3-ylsulfanyl)-propyl]-1,2,3,4-tetrahydroisoquinoline-7-yl}-propan-1-one (dihydrochloride)—compound Ia'-71 as dihydrochloride 20.1 4-Methyl-5-pyridin-2-yl-4H-[1,2,4]triazole-3-thiol 15 g of pyridine-2-carboxylic acid (121.8 mmol) were dissolved in 150 ml of dimethylformamide. At room temperature, 29.6 g (181.8 mmol) of carbonyldiimidazole were slowly added, during which gas was evolved. Reaction was allowed to take place at 100° C. for 30 min, and then 25.6 g (242.7 mmol) of 4-methyl-3-thiosemicarbazide were added, and the mixture was stirred at 100° C. for a further 2 h. The reaction mixture was mixed with 300 ml of water. After cooling in an ice bath, the precipitated crystals were filtered off with suction and washed with a little water. The crystals were taken up in 390 ml of 1M sodium bicarbonate solution and heated to reflux for 3 h.

Cooling was followed by neutralization with concentrated hydrochloric acid, filtration of the white crystals, washing with a little water and drying overnight at 50° C. 18.5 g of the title compound were obtained.

20.2 1-{2-[3-(4-Methyl-5-pyridin-2-yl-4H-[1,2,4]-triazol-3-ylsulfanyl)-propyl]-1,2,3,4-tetra-hydroisoquinoline-7-yl}-propan-1-one (dihydrochloride)

1.08 g (5.44 mmol) of 4-methyl-5-pyridin-2-yl-4H-[1,2,4] triazole-3-thiol, 0.135 g (5.44 mmol) of lithium hydroxide and 0.422 g (2.82 mmol) of sodium iodide were introduced into 14 ml of dimethylformamide and heated to 70° C. A solution of 1.5 g (5.44 mmol) of 1-[2-(3-chloropropyl)-1,2,3,4-tetrahydroisoquinoline-7-yl]-propan-1-one from step 1.4 in 6 ml of dry dimethylformamide was added dropwise thereto at a temperature of 70° C. over the course of 2 h, and the mixture was stirred at 90° C. for 30 min. The reaction mixture was concentrated in vacuo. The pale yellow oil obtained in this way was poured into 20 ml of saturated brine and 20 ml of water and then extracted three times with 30 ml of ethyl acetate.

The combined organic phases were dried over magnesium sulfate, filtered and concentrated. The crude product (2.8 g) obtained in this way was by means of and evaporated. The crude product (2.8 g) obtained in this way was purified by flash chromatography. (Eluents: 1. dichloromethane; 2. dichloromethane/methanol 98:2; 3. dichloromethane/methanol 30:1). To prepare the hydrochloride salt, the free base of the title compound obtained in this way (1.1 g) was dissolved in 20 ml of ethyl acetate, and 4N hydrogen chloride in dioxane was added to the solution. The white precipitate which separated out was filtered off with suction, washed with ether and dried. 1.0 g of the title compound was obtained as a white solid; [M+H]+=424.

Example 21

1-[2-(3-{[4-Methyl-5-(1H-pyrrol-2-yl)-4H-1,2,4-triazol-3-yl]thio}propyl)-2,3-dihydro-1H-isoindol-5-yl]propan-1-one hydrochloride The title compound was prepared in analogy to method 1.5 from 4-methyl-5-(1H-pyrrol-2-yl)-4H-1,2,4-triazole-3-thiol (1.43 mmol, 0.26 g) and 1-[2-(3-chloropropyl)-2,3-dihydro-1H-isoindol-5-yl]propan-1-one (1.43 mmol, 0.36 g; preparation in analogy to 1.4 from isoindoline as disclosed in WO 0125200). Yield: 0.11 g.

$^1$H-NMR (500 MHz, CDCl$_3$) δ ppm: 7.79 (d, 1H), 7.74 (s, 1H), 7.20 (d, 1H), 7.10 (s, 1H), 6.54 (s, 1H), 6.28 (m, 1H), 3.94 (s, 4H), 3.72 (s, 3H), 3.28 (t, 2H), 2.95 (q, 2H), 2.89 (t, 2H), 2.05 (quint., 2H), 1.20 (t, 3H).

Example 22

1-(2-{3-[(4-Methyl-5-phenyl-4H-1,2,4-triazol-3-yl)thio]propyl}-2,3-dihydro-1H-isoindol-5-yl)propan-1-one hydrochloride The title compound was prepared in analogy to method 1.5 from 4-methyl-5-phenyl-4H-1,2,4-triazole-3-thiol (1.43 mmol, 0.33 g) and 1-[2-(3-chloropropyl)-2,3-dihydro-1H-isoindol-5-yl]propan-1-one (1.43 mmol, 0.36 g; preparation in analogy to 1.4 from isoindoline as disclosed in WO 0125200). Yield: 0.24 g.

$^1$H-NMR (500 MHz, CDCl$_3$) δ ppm: 7.84-7.77 (m, 2H), 7.65-7.59 (m, 2H), 7.53-7.48 (m, 3H), 7.26 (d, 1H), 3.96 (s, 4H), 3.59 (s, 3H), 3.38 (t, 2H), 2.95 (q, 2H), 2.89 (t, 2H), 2.08 (quint., 2H), 1.20 (t, 3H).

Example 23

1-(2-{3-[(4-Methyl-5-pyridin-3-yl-4H-1,2,4-triazol-3-yl)thio]propyl}-2,3-dihydro-1H-isoindol-5-yl)propan-1-one The title compound was prepared in analogy to method 1.5 from 4-methyl-5-pyridin-3-yl-4H-1,2,4-triazole-3-thiol (1.43 mmol, 0.33 g) and 1-[2-(3-chloropropyl)-2,3-dihydro-1H-isoindol-5-yl]propan-1-one (1.43 mmol, 0.36 g; preparation in analogy to 1.4 from isoindoline as disclosed in WO 0125200). Yield: 0.04 g.

$^1$H-NMR (500 MHz, CDCl$_3$) δ ppm: 8.87 (s, br., 1H), 8.70 (s, br., 1H), 8.02 (m, 1H), 7.87-7.75 (m, 1H), 7.43 (m, 2H), 7.25 (m, 1H), 4.02 (s, 4H), 3.61 (s, 3H), 3.37 (t, 2H), 2.91 (m, 2H), 2.15 (t, 2H), 1.84 (m, sym., 2H), 1.20 (t, 3H).

Examples of Pharmaceutical Administration Forms

A) Tablets

Tablets of the following composition are compressed in a tablet press in a conventional way:

40 mg of substance of example 2
120 mg of corn starch
13.5 mg of gelatin
45 mg of lactose
2.25 mg of Aerosil® (chemically pure silica in submicroscopically fine distribution)
6.75 mg of potato starch (as 6% strength paste)

B) Sugar-coated Tablets 20 mg of substance of example 2
60 mg of core composition
70 mg of sugar-coating composition The core composition consists of 9 parts of corn starch, 3 parts of lactose and 1 part of vinylpyrrolidone/vinyl acetate 60:40 copolymer. The sugar-coating composition consists of 5 parts of sucrose, 2 parts of corn starch, 2 parts of calcium carbonate and 1 part of talc. The sugar-coated tablets produced in this way are subsequently provided with an enteric coating.

Biological Investigations—Receptor Binding Studies

The substance to be tested was dissolved either in methanol/Chremophor® (BASF-AG) or in dimethyl sulfoxide and then diluted with water to the desired concentration.

Dopamine $D_3$ Receptor:

The mixture (0.250 ml) is composed of membranes from ~$10^6$ HEK-293 cells with stably expressed human dopamine D3 receptors, 0.1 nM [$^{125}$I]-iodosulpride and incubation buffer (total binding) or with addition of test substance (inhibition plot) or 1 μM spiperone (nonspecific binding). Triplicate mixtures were carried out.

The incubation buffer contained 50 mM Tris, 120 mM NaCl, 5 mM KCl, 2 mM $CaCl_2$, 2 mM $MgCl_2$ and 0.1% bovine serum albumin, 10 μM quinolone, 0.1% ascorbic acid (prepared fresh each day). The buffer was adjusted to pH 7.4 with HCl.

Dopamine $D_2(L)$ Receptor:

The mixture (1 ml) was composed of membranes from ~$10^6$ HEK-293 cells with stably expressed human dopamine $D_2$(L) receptors (long isoform) and 0.01 nM [$^{125}$I]-iodospiperone and incubation buffer (total binding) or with addition of test substance (inhibition plot) or 1 μM haloperidol (nonspecific binding). Triplicate mixtures were carried out.

The incubation buffer contained 50 mM Tris, 120 mM NaCl, 5 mM KCl, 2 mM $CaCl_2$, 2 mM $MgCl_2$ and 0.1% bovine serum albumin. The buffer was adjusted to pH 7.4 with HCl.

Measurement and Evaluation:

After incubation at 25° C. for 60 minutes, the mixtures were filtered under vacuum through Wathman GF/B glass fiber filters using a cell harvester. The filters were transferred by a filter transfer system into scintillation vials. After addition of 4 ml of Ultima Gold® (Packard), the samples were shaken for one hour and then the radioactivity was calculated in a beta counter (Packard, Tricarb 2000 or 2200CA). The cp values were converted into dpm by means of a standard quench series with the aid of the instrument's own program.

Evaluation of the inhibition plots took place by iterative nonlinear regression analysis using the statistical analysis system (SAS) similar to the "LIGAND" program described by Munson and Rodbard.

In these assays, the inventive compounds show very good affinities for the $D_3$ receptor (<100 nmolar, in particular <50 nM) and bind selectively to the $D_3$ receptor. The results of the binding assays are indicated in table 2.

TABLE 2

| Compound No. | Ki ($D_3$) [nM] | Ki ($D_2$)/Ki ($D_3$) |
|---|---|---|
| Ia'-1 | 11.4 | 133 |
| Ia'-3 | 19.3 | 40 |
| Ia'-4 | 4.5 | 80 |
| Ia'-12 | 10.7 | 90 |

TABLE 2-continued

| Compound No. | Ki ($D_3$) [nM] | Ki ($D_2$)/Ki ($D_3$) |
|---|---|---|
| Ia'-15 | 4.4 | 103 |
| Ia'-18 | 22.4 | 48 |
| Ia'-19 | 8.6 | 149 |
| Ia'-25 | 4.4 | 90 |
| Ia'-39 | 18.8 | 37 |
| Ia'-46 | 21.7 | 94 |
| Ia'-57 | 2.6 | 59 |
| Ia'-58 | 25.5 | 39 |
| Ia'-60 | 30.3 | 37 |
| Ia'-63 | 40.3 | 38 |
| Ia'-68 | 14.9 | 56 |
| Ia'-64 | 20.2 | 46 |
| Ib'-25 | 21.4 | 126 |
| Ib'-65 | 40.0 | 49 |

Investigation of the cerebral availability and the oral bioavailability

The test substances were administered to male Wistar rats in parallel experiments in each case intravenously (tail vein, 2 mg/kg of body weight) and orally (gavage, 10 mg/kg of body weight). The test compound was dissolved in water with up to 4% by volume of DMSO and/or ethanol for intravenous administration and suspended in 4% by weight aqueous hydroxypropyl-cellulose solution for oral administration. After various times (intravenous: 5 min, 15 min, 30 min, 2 h, 8 h and 24 h; oral: 15 min, 30 min, 2 h, 8 h and 24 h) after the administration, a blood sample or brain tissue were taken from 2 rats in each case. The concentration of the test compound in the blood plasma and in the brain tissue (plasma and brain) was determined in a conventional way by coupled liquid chromatography/mass spectroscopy or by HPLC. The area under the concentration-time plot for brain ($AUC_{brain}$) and for plasma ($AUC_{iV}$, $AUC_{oral}$) were by means of the trapezoidal method from the results obtained [$((t_n-t_{n-1})\times(c_n+c_{n-1})/2)$] calculated, in which $t_n$ is the time of determination and $t_{n-1}$ is the preceding time of determination, and $c_n$ and $c_{n-1}$ are respectively the concentrations at time $t_n$ and $t_{n-1}$]. The maximum concentration of the active ingredients in brain tissue $c_{max}$ brain, the value of $AUC_{brain}$, and the $AUC_{brain}/AUC_{plasma}$ ratio is a measure of the cerebral availability of the active substance. In addition, the bioavailability F of the active ingredient was calculated in a manner known per se from the data ($AUC_{oral}/AUC_{iv}$, in %). The tested active ingredients and the pharmacokinetic data are indicated in table 3. The meanings of Ar and R in the formula indicated below are those indicated in table 3.

TABLE 3

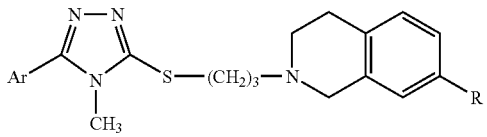

| No. | Ar | R | $c_{max}$ (brain)* [ng/g] | $AUC_{brain}$* [ng h/g] | $AUC_{brain}/AUC_{plasma}$ | F [%] |
|---|---|---|---|---|---|---|
| A | 1-Methyl-pyrrol-2-yl | $SO_2$-Piperidinyl | b.l. | | n.k | 3 |
| B | 1-Methyl-pyrrol-2-yl | Methoxy | 87 | 228 | 2.1 | 3 |

TABLE 3-continued

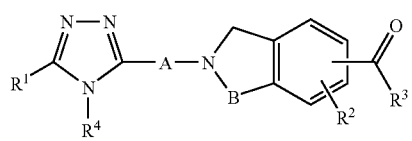

| No. | Ar | R | $c_{max}$ (brain)* [ng/g] | $AUC_{brain}$* [ng h/g] | $AUC_{brain}/$ $AUC_{plasma}$ | F [%] |
|---|---|---|---|---|---|---|
| Ia'-15 | 1-Methyl-pyrrol-2-yl | C(O)-Ethyl | 686 | 2903 | 0.3 | 100 |
| Ia'-12 | 1-Methyl-pyrrol-2-yl | C(O)-Phenyl | 130 | 306 | 0.2 | 10 |

*from oral experiments,
b.l.: below limits of detection,
n.k: not known,
F: bioavailability
A: Example 35 of WO 00/42306 (free base)
B: Example 594 of WO 00/42306 (hydrochloride)
Ia'-15 (hydrochloride)
Ia'-12 (hydrochloride)

It emerged that the inventive compounds have a distinctly higher cerebral availability and bioavailability than comparative compounds not corresponding to formula I.

The invention claimed is:

1. A triazole compound of the formula I (I)

in which

A is $C_4$-$C_{10}$-alkylene or $C_3$-$C_{10}$-alkylene which includes at least one group Z which is selected from O, S, $NR^5$, $CONR^5$, COO and CO, where alkylene may also have a $C_3$-$C_6$-cycloalkylene group and/or a double or triple bond, B is $CH_2$ or $CH_2$-$CH_2$;

$R^1$ is an aromatic radical which is selected from phenyl and a 5- or 6-membered heteroaromatic radical having 1, 2, 3 or 4 heteroatoms which are selected independently of one another from O, N and S, where the aromatic radical may have one or more substituents which are selected independently of one another from $C_1$-$C_6$-alkyl which is optionally substituted by OH, $C_1$-$C_4$-alkoxy, halogen or phenyl, or $C_2$-$C_6$-alkenyl, $C_2$-$C_6$-alkynyl, $C_3$-$C_6$-cycloalkyl which is optionally substituted by halogen or $C_1$-$C_4$-alkyl, or halogen, CN, $OR^6$, $COOR^6$, $NR^7R^8$, $NO_2$, $SR^9$, $SO_2R^9$, $SO_2NR^7R^8$, $COR^{10}$, and phenyl which is optionally substituted by one or two radicals which are selected independently of one another from $C_1$-$C_4$-alkyl, $C_1$-$C_4$-alkoxy, $NR^7R^8$, CN, $CF_3$, $CHF_2$ or halogen, where phenyl and the heteroaromatic radical may also be fused to a 5 or 6-membered, aromatic or nonaromatic carbocycle;

$R^2$ is H, $C_1$-$C_6$-alkyl which is optionally substituted by OH, $C_1$-$C_4$-alkoxy, $C_1$-$C_4$-alkylthio, halogen or phenyl, or OH, $C_1$-$C_6$-alkoxy, $OCF_3$, $OCHF_2$, $OSO_2CF_3$, SH, $C_1$-$C_6$-alkylthio, $C_2$-$C_6$-alkenyl, $C_2$-$C_6$-alkynyl, halogen, CN or $NO_2$;

$R^3$ is $C_2$-$C_{10}$-alkyl, $C_1$-$C_6$-haloalkyl, $C_1$-$C_{10}$-alkyl which is substituted by $C_1$-$C_4$-alkoxy, $C_1$-$C_4$-alkylthio or phenyl which may in turn have one, two or three substituents selected from $C_1$-$C_4$-alkyl, $C_1$-$C_4$-haloalkyl, halogen, CN, $OR^6$, $COOR^6$, $NR^7R^8$, $NO_2$, $SR^9$, $SO_2R^9$, $SO_2NR^7R^8$, $COR^{10}$ and halogen, is $C_3$-$C_6$-cycloalkyl which is optionally substituted by halogen or $C_1$-$C_4$-alkyl, or is an aromatic radical which is selected from phenyl, naphthyl and a 5- or 6-membered heteroaromatic radical having 1, 2, or 3 heteroatoms which are selected independently of one another from O, N and S, where the aromatic radical may have one or two substituents which are selected independently of one another from $C_1$-$C_6$-alkyl, $C_1$-$C_6$-haloalkyl, $C_1$-$C_6$-alkoxy, halogen, CN, $COOR^6$, $NR^7R^8$, $NO_2$, $SO_2R^9$, $SO_2NR^7R^8$, $COR^{10}$, $CF_3$, $CHF_2$ or halogen, where $R^3$ may also be methyl if $R^1$ is an optionally substituted heteroaromatic radical;

$R^4$ is H, $C_1$-$C_6$-alkyl which is optionally substituted by OH, $C_1$-$C_4$-alkoxy or phenyl, or $C_1$-$C_6$-haloalkyl, $C_3$-$C_6$-cycloalkyl which is optionally substituted by $C_1$-$C_4$-alkyl or halogen, or phenyl;

$R^5$ is H, $C_1$-$C_6$-alkyl which is optionally substituted by OH, $C_1$-$C_4$-alkoxy or phenyl, or $C_1$-$C_6$-haloalkyl, phenyl or a $COR^{11}$ group;

$R^6$ to $R^{10}$ are independently of one another H, $C_1$-$C_6$-alkyl which is optionally substituted by OH, $C_1$-$C_4$-alkoxy or phenyl, or $C_1$-$C_6$-haloalkyl or phenyl, where $R^8$ may also be a $COR^{11}$ group in which $R^{11}$ has one of the meanings mentioned for $R^4$;

$R^7$ may also form together with $R^8$ a 5- or 6-membered saturated or unsaturated carbocycle which may have a heteroatom selected from O, S, N and $NR^{12}$ as ring member, where $R^{12}$ is hydrogen or $C_1$-$C_4$-alkyl, or a physiologically tolerated salt of this compound.

2. The compound as claimed in claim 1 in which B is $CH_2CH_2$.

3. The compound as claimed in claim 1 in which A is $C_4$-$C_{10}$-alkylene or Z-$C_3$-$C_{10}$-alkylene, where alkylene may have a double bond, Z is bonded to the triazole ring and is selected from O, S, COO, $NR^5$ and CO.

4. The compound as claimed in claim 3 in which A is a group S—($C_3$-$C_{10}$-alkylene) in which alkylene may have a double bond.

5. The compound as claimed in claim 1 in which $R^2$ is H.

6. The compound as claimed in claim 1 in which $R^1$ is phenyl which is unsubstituted or has one or two substituents which are selected independently of one another from $C_1$-$C_6$-alkyl, OH, $C_1$-$C_6$-alkoxy, phenyl, CN and halogen and/or which may be fused to a 6-membered aromatic carbocycle.

7. The compound as claimed in claim 1 in which $R^1$ is a heteroaromatic radical which is selected from thienyl, furanyl, tetrazolyl, pyrrolyl, benzothienyl, indolyl, benzothiazolyl, pyridyl or pyrazinyl, where the aromatic radical may be substituted in the manner indicated in claim 1.

8. The compound as claimed in claim 7, in which $R^1$ is pyrrolyl which optionally has 1 or 2 substituents selected from $C_1$-$C_4$-alkyl and $C_3$-$C_6$-cycloalkyl.

9. The compound as claimed in claim 1 in which $R^3$ is $C_2$-$C_{10}$-alkyl, $C_3$-$C_6$-cycloalkyl, benzyl or phenyl which may have one or two substituents which are selected independently of one another from $C_1$-$C_6$-alkyl, $C_1$-$C_6$-alkoxy, halogen, CN, $NO_2$, $CF_3$, $CHF_2$ or halogen.

10. The compound as claimed in claim 1 of the formula Ia

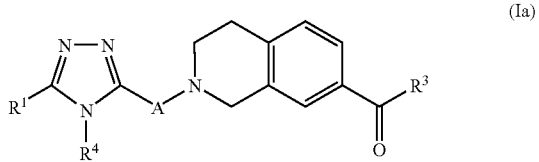

(Ia)

in which A, $R^1$ $R^3$ and $R^4$ have the meanings indicated above.

11. The compound as claimed in claim 10 in which

A is $C_4$-$C_{10}$-alkylene or Z-$C_3$-$C_{10}$-alkylene, where alkylene may have a double bond, Z is bonded to the triazole ring and is selected from O, S, COO, CONR$^5$, NR$^5$ and CO;

$R^1$ is an aromatic radical which is selected from phenyl, thienyl, furanyl, tetrazolyl, pyrrolyl, benzothienyl, indolyl, benzothiazolyl, pyridyl or pyrazinyl, where the aromatic radical may be substituted in the manner indicated in claim 1;

$R^3$ is $C_2$-$C_{10}$-alkyl, $C_3$-$C_6$-cycloalkyl, benzyl or phenyl which may have one or two substituents which are selected independently of another from $C_1$-$C_6$-alkyl, $C_1$-$C_6$-alkoxy, halogen, CN, $NO_2$, $CF_3$, $CHF_2$ or halogen, where $R^3$ may also be methyl if $R^1$ is not optionally substituted phenyl, and $R^4$ is hydrogen, $C_1$-$C_6$-alkyl or $C_3$-$C_6$-cycloalkyl.

12. The compound as claimed in claim 1 in which $R^1$ is pyrrolyl which optionally has 1 or 2 substituents selected from $C_1$-$C_4$-alkyl and $C_3$-$C_6$-cycloalkyl.

13. The compound as claimed in claim 10 of the formula Ia in which A is a group S—($C_3$-$C_{10}$-alkylene) in which alkylene may have a double bond.

14. The compound as claimed in claim 11 in which $R^2$ is methyl, A is a group Z'-$(CH_2)_k$ where Z' is bonded to the triazole ring and is oxygen, sulfur or $CH_2$, k is 3 or 4, $R^1$ is phenyl, 4-fluorophenyl, pyrrol-2-yl, 1-methylpyrrol-2-yl, 2-thienyl, 3-thienyl, benzothien-2-yl, 2-furyl, 3-furyl, benzothiazol-2-yl, 2-pyridinyl, 3-pyridinyl, 4-pyridinyl or 2-pyrazinyl, and $R^3$ is $C_2$-$C_4$-alkyl or phenyl which may be substituted once or twice by $C_1$-$C_4$-alkyl, $C_1$-$C_4$-alkoxy, $CF_3$, $CHF_2$ or halogen, or may also be methyl if $R^1$ is different from phenyl.

15. A pharmaceutical composition comprising at least one compound of the formula I as claimed in claim 1, where appropriate together with physiologically acceptable carriers and/or excipients.

16. A method for the treatment of disorders which respond to influencing of dopamine $D_3$ receptors, selected from Parkinson's disease, schizophrenia, cognitive disturbances, depression, axiety, addiction, kidney function disturbances and eating disturbances, comprising administering to a patent in need of such treatment an effective amount of at least one compound of claim 1.

* * * * *